US012558519B2

(12) United States Patent
Heye

(10) Patent No.: US 12,558,519 B2
(45) Date of Patent: Feb. 24, 2026

(54) INSTRUMENT WITH A COUNTER-PIVOTING MECHANISM

(71) Applicant: Intuitive Surgical Operations, Inc., Sunnyvale, CA (US)

(72) Inventor: Isabelle Heye, San Francisco, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 513 days.

(21) Appl. No.: 18/295,618

(22) Filed: Apr. 4, 2023

(65) Prior Publication Data

US 2023/0310807 A1    Oct. 5, 2023

Related U.S. Application Data

(60) Provisional application No. 63/327,472, filed on Apr. 5, 2022.

(51) Int. Cl.
A61M 25/01        (2006.01)
A61B 34/00        (2016.01)

(52) U.S. Cl.
CPC ......... A61M 25/0147 (2013.01); A61B 34/70 (2016.02); A61B 34/71 (2016.02)

(58) Field of Classification Search
CPC ..... A61M 25/0147; A61B 34/70; A61B 34/71
See application file for complete search history.

(56) References Cited

U.S. PATENT DOCUMENTS

| | | | |
|---|---|---|---|
| 7,942,868 B2 | 5/2011 | Cooper et al. | |
| 9,179,832 B2 * | 11/2015 | Diolaiti ................. | A61B 1/008 |
| 9,259,274 B2 * | 2/2016 | Prisco ................... | A61B 34/37 |
| 9,662,176 B2 * | 5/2017 | Cooper ................. | A61B 34/37 |
| 11,033,716 B2 * | 6/2021 | Schlesinger .......... | A61B 34/71 |
| 2014/0148673 A1 | 5/2014 | Bogusky | |

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

*Primary Examiner* — Dung T Ulsh
(74) *Attorney, Agent, or Firm* — Haynes & Boone, LLP.

(57) ABSTRACT

An instrument includes an elongate shaft, a counter-pivoting mechanism, and control cables. A first joint of the counter-pivoting mechanism, having a first link, is coupled to the elongate shaft, and a second joint, having a second link, is disposed distally of the first joint. An elongate tube is disposed between the first joint and the second joint. Constraint cables extend linearly between the first and second joints within first grooves formed in an outer surface the elongate tube. The control cables wrap helically around the elongate tube within second grooves formed in the outer surface. The joints are coupled by the constraint cables such that as the counter-pivoting mechanism is manipulated by the control cables, the first joint pivots in a first direction as the second joint pivots in an opposing second direction to maintain the first and second links in a parallel orientation.

20 Claims, 15 Drawing Sheets

INSTRUMENT WITH A COUNTER-PIVOTING MECHANISM

CROSS-REFERENCED APPLICATIONS

This application claims priority to and benefit of U.S. Provisional Application No. 63/327,472, filed Apr. 5, 2022 and entitled "Instrument With a Counter-Pivoting Mechanism," which is incorporated by reference herein in its entirety.

FIELD

The present disclosure is directed to systems and methods for conducting a medical or non-medical procedure, and more particularly to a tool with a counter-pivoting mechanism.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical instruments to reach a target tissue location. Minimally invasive medical instruments include instruments such as therapeutic, diagnostic, biopsy, and surgical instruments. Medical instruments may be inserted into anatomic passageways and navigated toward a region of interest within a patient anatomy.

Some medical instruments include a parallel motion mechanism to translate a portion of the instrument while maintaining an orientation of the portion of the instrument. An existing parallel motion mechanism construction includes two coaxial tubes with cables routed between the inner tube and the outer tube as described in U.S. Pat. No. 7,942,868 (filed Jun. 13, 2007) (disclosing "Surgical Instrument with Parallel Motion Mechanism") which is incorporated by reference herein in its entirety. Such a design has properties which may be undesirable in some procedures.

Instruments with improved counter-pivoting mechanisms are needed to enhance medical and non-medical procedures.

SUMMARY

Consistent with some examples, an instrument may comprise an elongate shaft, a counter-pivoting mechanism, and a plurality of control cables extending through the elongate shaft and configured to control manipulation of the counter-pivoting mechanism. The elongate shaft may have a proximal portion and a distal portion. The counter-pivoting mechanism may include a first joint coupled to the distal portion of the elongate shaft, the first joint comprising a first link, and a second joint disposed distally of the first joint, the second joint comprising a second link. The counter-pivoting mechanism may further comprise an elongate tube disposed between the first joint and the second joint and having a central lumen extending along a longitudinal axis of the elongate tube. A plurality of constraint cables may extend linearly between the first and second joints within a plurality of first grooves formed in an outer circumferential surface of a wall of the elongate tube. The plurality of control cables may wrap helically around at least a portion of the elongate tube within a plurality of second grooves formed in the outer circumferential surface of the wall of the elongate tube. The first and second joints may be coupled by the plurality of constraint cables such that as the counter-pivoting mechanism is manipulated by the plurality of control cables, the first joint pivots in a first direction as the second joint pivots in a second direction opposite the first direction while the first link and the second link are maintained in a parallel orientation.

In some examples, each of the plurality of control cables may be secured to the second joint. An instrument may further include a third joint coupled to the first joint and a fourth joint coupled to the second joint. The first and second joints may be configured to pivot in a pitch direction and the third and fourth joints may be configured to pivot in a yaw direction. The plurality of control cables may include a set of pitch control cables and a set of yaw control cables.

In some examples, each control cable of the plurality of control cables may exit the wall of the elongate tube at a position circumferentially offset approximately 180° with respect to the longitudinal axis from a position in which each respective control cable enters the wall of the elongate tube. In some examples, the plurality of second grooves may be formed deeper into the wall than the plurality of first grooves such that the plurality of constraint cables is disposed radially outward from the plurality of control cables within the elongate tube or the plurality of first grooves may be formed deeper into the wall than the plurality of second grooves such that the plurality of constraint cables is disposed radially inward from the plurality of control cables within the elongate tube.

In some examples, an outer diameter of the elongate tube may be less than about 5 mm. A maximum width of the central lumen may be greater than about 2.8 mm. In this regard, a ratio of a cross-sectional area of the central lumen to a cross-sectional area of the elongate tube may be greater than 1:2.

In some examples, an instrument may include an end effector disposed distally of the counter-pivoting mechanism. The end effector may optionally include a wrist joint. A plurality of wrist control cables may extend through the central lumen of the elongate tube and be secured to the wrist joint. The plurality of wrist control cables may be disposed within a plurality of coil pipes extending through the central lumen of the elongate tube. The end effector may comprise a gripper and the plurality of wrist control cables may include at least four cables configured to control pitch, yaw, and grip of the end effector. The end effector may comprise an electrocautery blade or an ablation tool, and a conductor wire may extend through the central lumen of the elongate tube.

In some examples, an instrument may include a shape sensor extending through the first and second joints.

Consistent with some examples, an instrument may comprise an elongate shaft having a proximal portion and a distal portion, a counter-pivoting mechanism, and a plurality of control cables extending through the elongate shaft and configured to control manipulation of the counter-pivoting mechanism. The counter-pivoting mechanism may comprise a first joint coupled to the distal portion of the elongate shaft, the first joint comprising a first link, a second joint disposed distally of the first joint, the second joint comprising a second link, an elongate tube disposed between the first joint and the second joint and having a central lumen extending along a longitudinal axis of the elongate tube, and a plurality of constraint cables extending between the first and second joints within a plurality of channels formed in a wall of the elongate tube. The plurality of control cables may wrap helically around at least a portion of the elongate tube within a plurality of grooves formed in an outer circumferential surface of the wall of the elongate tube. The first and second joints may be coupled by the plurality of constraint cables such that as the counter-pivoting mechanism is manipulated by the plurality of control cables, the first joint pivots in a first direction as the second joint pivots in a second direction opposite the first direction while the first link and the second link are maintained in a parallel orientation.

In some examples, the plurality of channels may comprise linear lumens extending through the wall of the elongate tube. In some examples, the plurality of channels may extend within the central lumen. In some examples, the plurality of channels may comprise grooves formed in an inner surface of the wall of the elongate tube.

Consistent with some examples, a method of controlling an instrument may include manipulating at least one control cable of a plurality of control cables extending through an elongate shaft of the instrument, the instrument having a proximal portion, a distal portion, and a counter-pivoting mechanism. The counter-pivoting mechanism may comprise a first joint coupled to the distal portion of the elongate shaft, the first joint comprising a first link, a second joint disposed distally of the first joint, the second joint comprising a second link, an elongate tube disposed between the first joint and the second joint and having a central lumen extending along a longitudinal axis of the elongate tube, and a plurality of constraint cables extending linearly between the first and second joints within a plurality of first grooves formed in an outer circumferential surface of a wall of the elongate tube. The at least one control cable may extend through at least one of a plurality of helically wrapped second grooves formed in an outer circumferential surface of a wall of the elongate tube. Manipulating the at least one control cable may cause the first joint to pivot in a first direction and the second joint to pivot in a second direction opposite the first direction while the first link and the second link are maintained in a parallel orientation by the plurality of constraint cables.

Other examples include corresponding computer systems, apparatus, and computer programs recorded on one or more computer storage devices, each configured to perform the actions of any methods described herein.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

Figure 1:
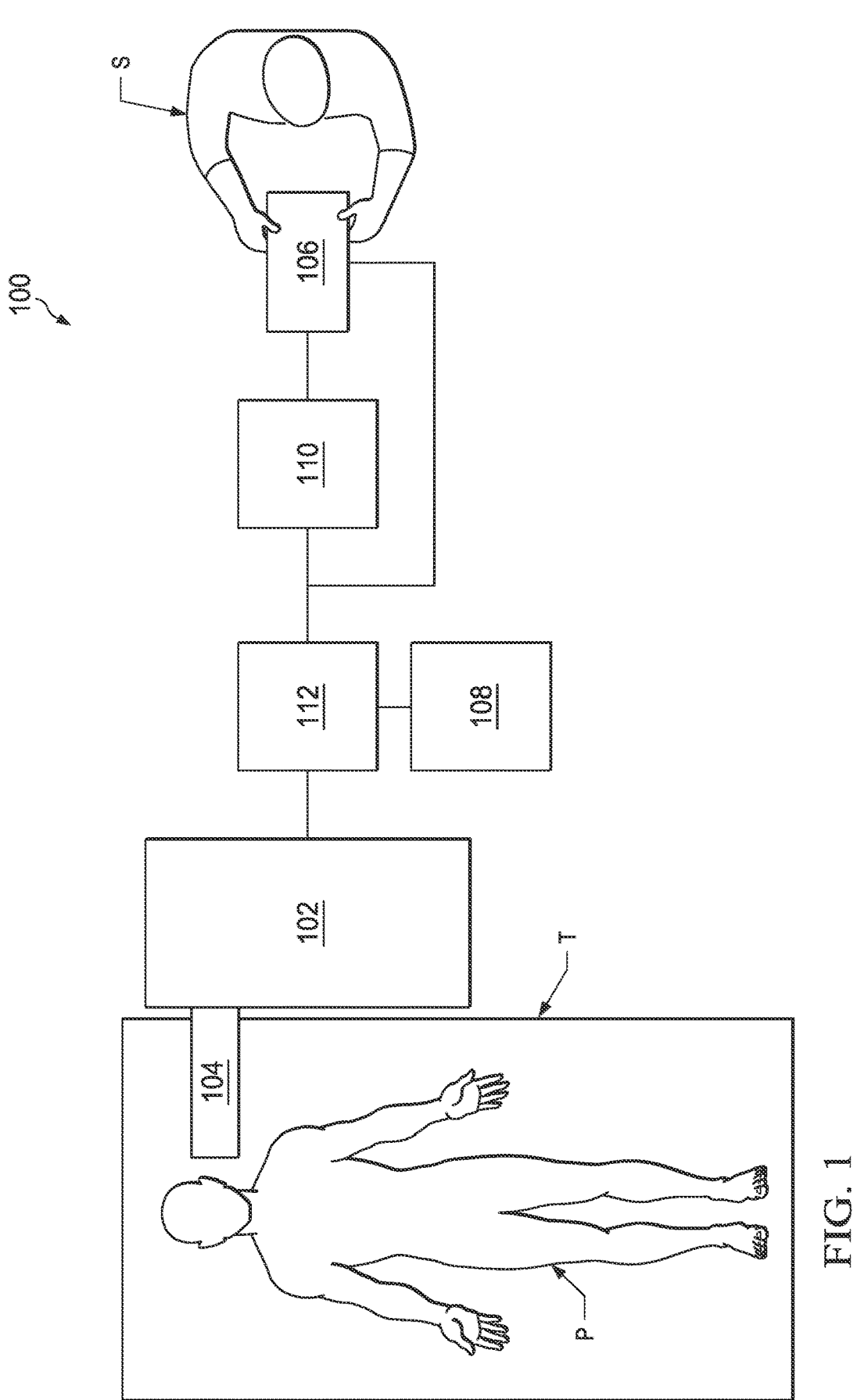
FIG. 1 is a diagram of a teleoperational system, in accordance with the present disclosure.

Examples of the present disclosure and their advantages are best understood by referring to the detailed description that follows. It should be appreciated that like reference numerals are used to identify like elements illustrated in one or more of the figures, wherein showings therein are for purposes of illustrating examples of the present disclosure and not for purposes of limiting the same.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances, well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

A counter-pivoting mechanism may be positioned between an instrument's end effector and elongate shaft. The counter-pivoting mechanism may be designed to maintain a parallel arrangement between a proximal link and a distal link disposed on either side of the counter-pivoting mechanism during bending of the instrument at the counter-pivoting mechanism. This may allow a position of the end effector and/or wrist to be translated while maintaining the orientation of the end effector and/or wrist with respect to a portion of the elongate shaft.

The present disclosure relates to a counter-pivoting mechanism for an instrument with a design that may facilitate use in a teleoperational or robotically-assisted surgical platform by reducing an outer diameter of the counter-pivoting mechanism and/or increasing an inner diameter of a central lumen or working channel. This may be accomplished, for example, by disposing control and/or constraint cables for the counter-pivoting mechanism in grooves or channels formed in a wall of the counter-pivoting mechanism.

Referring to FIG. 1 of the drawings, a teleoperational system for use in, for example, surgical, diagnostic, therapeutic, biopsy, or non-medical procedures (which may collectively be referred to as "surgical" herein), is generally indicated by the reference numeral 100. As shown in FIG. 1, the teleoperational system 100 generally includes a teleoperational manipulator assembly 102 for operating a medical instrument system 104 in performing various procedures, for example, a medical procedure on a patient P. The medical instrument system 104 may include one or more steerable instruments and/or one or more passive instruments. One or more instruments of the medical instrument system 104 may be configured to be positioned within a working channel or lumen of one or more other instruments of the medical instrument system 104. In some examples, one or more surgical instruments or tools may be positionable within one or more working channels of an instrument such as a catheter or endoscope of the medical instrument system 104. The manipulator assembly 102 is mounted to or near a patient support table T which may be located in a surgical operating room or other medical setting. An operator input system 106 allows the operator (e.g., a clinician, surgeon, or other personnel) S to view the interventional site and to control the manipulator assembly 102. A single manipulator assembly 102, medical instrument system 104, and operator input system 106 is shown in FIG. 1. However, it should be understood that various teleoperated systems may have a plurality of manipulator assemblies, medical instrument systems (each including one or more medical instruments), operator input systems, or combination thereof.

The operator input system 106 may be located at a user control system which is usually located in the same room as patient support table T. However, it should be understood that the operator S can be located in a different room or a completely different building or be geographically remote from the patient P. Operator input system 106 generally includes one or more control devices for controlling the manipulator assemblies 102. The control devices may include any number of a variety of input devices or sensors, such as joysticks, trackballs, data gloves, trigger-guns, hand-operated controllers, eye tracking devices, voice recognition devices, body motion or presence sensors, or the like. In some embodiments, the control devices will be provided with the same degrees of freedom as one or more associated medical instruments systems (such as medical instrument system 104) to provide the operator with telepresence, or the perception that the control devices are integral with the medical instrument systems so that the operator has a sufficiently strong sense of directly controlling the medical instrument systems. In other embodiments, the control devices may have more or fewer or different degrees of freedom than the one or more associated medical instrument systems (such as medical instrument system 104) and still provide the operator with telepresence. In some embodiments, the control devices are manual input devices which move with six degrees of freedom, and which may also include an actuatable handle for actuating instruments (for example, for closing grasping jaws, applying an electrical potential to an electrode, delivering a medicinal treatment, or the like).

The teleoperational manipulator assembly 102 supports the medical instrument system 104 and may include a kinematic structure of one or more non-servo and/or servo-controlled links (e.g., one or more links that may be manually or robotically positioned and locked in place, generally referred to as a set-up structure) and a teleoperational manipulator. The teleoperational manipulator assembly 102 includes a plurality of actuators or motors that drive inputs on one or more instruments of the medical instrument system 104 in response to commands from the control system (e.g., a control system 112). The motors include drive systems that when coupled to the medical instrument system 104 may advance the instrument(s) of the medical instrument system 104 into a naturally or surgically created anatomic orifice. Other motorized drive systems may move the distal end of the instrument(s) of the medical instrument system 104 in multiple degrees of freedom, which may include three degrees of translational motion (e.g., translational motion along the X, Y, Z Cartesian axes) and in three degrees of rotational motion (e.g., rotation about the X, Y, Z Cartesian axes). Additionally, the motors can be used to actuate an articulable end effector of an instrument for grasping tissue in the jaws of a biopsy device or the like. Motor position or speed sensors such as resolvers, encoders, potentiometers, and other mechanisms may provide sensor data to the teleoperational assembly describing the rotation and orientation of the motor shafts. This position sensor data may be used to determine motion of the objects manipulated by the motors.

The teleoperational system 100 also includes a sensor system 108 with one or more sub-systems for receiving information about the sub-assemblies of the teleoperational system 100 including instruments of the teleoperational manipulator assembly 102. Such sub-systems may include at least one of a position/location sensor system (e.g., an electromagnetic (EM) sensor system); a shape sensor system for determining the position, orientation, speed, velocity, pose, and/or shape of at least a portion of an instrument of the medical instrument system 104, such as a flexible steerable body or a rigid instrument body with or without joints; a visualization system for capturing images from the distal end of an instrument; other sensor systems based on various sensor technologies; or a combination thereof.

In some examples, a visualization system (e.g., visualization system 231 of FIG. 2A) may include a viewing scope assembly that records a concurrent or real-time image of the surgical site and provides the image to the operator (e.g., clinician or surgeon or other personnel) S. The concurrent image may be, for example, a two or three dimensional image captured by an endoscope positioned within the surgical site. In this embodiment, the visualization system includes endoscopic components that may be integrally or removably coupled to one or more instruments of the medical instrument system 104. However, in alternative embodiments, a separate endoscope, attached to a separate manipulator assembly may be used with the medical instrument system 104 to image the surgical site. The visualization system may be implemented as hardware, firmware, software or a combination thereof which interact with or are otherwise executed by one or more computer processors, which may include the processors of a control system 112 (described below). The processors of the control system 112 may execute instructions comprising instruction corresponding to processes disclosed herein.

The teleoperational system 100 also includes a display system 110 for displaying an image or representation of the surgical site and/or medical instrument system(s) 104 generated by sub-systems of the sensor system 108. The display system 110 and the operator input system 106 may be oriented so the operator can control the medical instrument system 104 and the operator input system 106 with the perception of telepresence.

The display system 110 may also display an image of the surgical site and medical instruments (e.g., instruments of medical instrument system 104) captured by the visualization system. The display system 110 and the control devices may be oriented such that the relative positions of the imaging device in the scope assembly and the medical instruments are similar to the relative positions of the operator's eyes and hands so the operator can manipulate the medical instrument system 104 and the hand control as if viewing the workspace in substantially true presence. By true presence, it is meant that the presentation of an image is a true perspective image simulating the viewpoint of an operator that is physically manipulating the medical instrument system 104.

Alternatively or additionally, the display system 110 may present images of the surgical site recorded pre-operatively or intra-operatively and/or a virtual navigational image. Additional details of such information suitable for display are provided in International Pat. Pub. No. WO2018/132386 (filed Jan. 9, 2018) (disclosing "Systems and Methos for Using a Robotic Medical System") and U.S. Pat. App. Pub. No. 2012/0289777 (filed May 13, 2011) (disclosing "Medical System Providing Dynamic Registration of a Model of an Anatomic Structure for Image-Guided Surgery") which are incorporated by reference herein in their entirety.

The teleoperational system 100 also includes a control system 112. The control system 112 includes at least one memory and at least one computer processor (not shown), and in some embodiments typically a plurality of processors, for effecting control between the medical instrument system 104, the operator input system 106, the sensor system 108, and the display system 110. The control system 112 also includes programmed instructions (e.g., a computer-readable medium storing the instructions) stored on non-transitory processor readable storage medium to implement some or all of the methods described in accordance with aspects disclosed herein, including instructions for providing information to the display system 110. While control system 112 is shown as a single block in the simplified schematic of FIG. 1, the control system 112 may include two or more data processing circuits with one portion of the processing optionally being performed on or adjacent the teleoperational manipulator assembly 102, another portion of the processing being performed at the operator input system 106, and the like. Any of a wide variety of centralized or distributed data processing architectures may be employed.

Similarly, the programmed instructions may be implemented as a number of separate programs or subroutines, or they may be integrated into a number of other aspects of the teleoperational systems described herein. In one embodiment, control system 112 supports one or more wired or wireless communication protocols. Wireless communications protocols include examples such as Bluetooth, IrDA, HomeRF, IEEE 802.11, DECT, and Wireless Telemetry.

In some embodiments, control system 112 may include one or more servo controllers that receive force and/or torque feedback from one or more medical instruments (such as those of medical instrument system 104). Responsive to the feedback, the servo controllers transmit signals to the operator input system 106. The servo controller(s) may also transmit signals instructing teleoperational manipulator assembly 102 to move a medical instrument which extends into an internal surgical or therapeutic site within the patient body via openings in the body. Any suitable conventional or specialized servo controller may be used. A servo controller may be separate from, or integrated with, teleoperational manipulator assembly 102. In some embodiments, the servo controller and teleoperational manipulator assembly 102 are provided as part of a teleoperational arm cart configured to be positioned adjacent to the patient's body during a surgical procedure.

The teleoperational system 100 may further include optional operation and support systems (not shown) such as illumination systems, steering control systems, irrigation systems, suction systems, cautery or energy application system, other systems, or combinations thereof. In alternative embodiments, the teleoperational system 100 may include more than one teleoperational manipulator assembly 102 and/or more than one operator input system 106. The exact number of teleoperational manipulator assemblies will depend on the surgical procedure and the space constraints within the operating room, among other factors. The operator input systems may be collocated or they may be positioned in separate locations that are geographically close or remote from each other. Multiple operator input systems allow more than one operator to control one or more manipulator assemblies in various combinations.

Figures 2A, 2B:
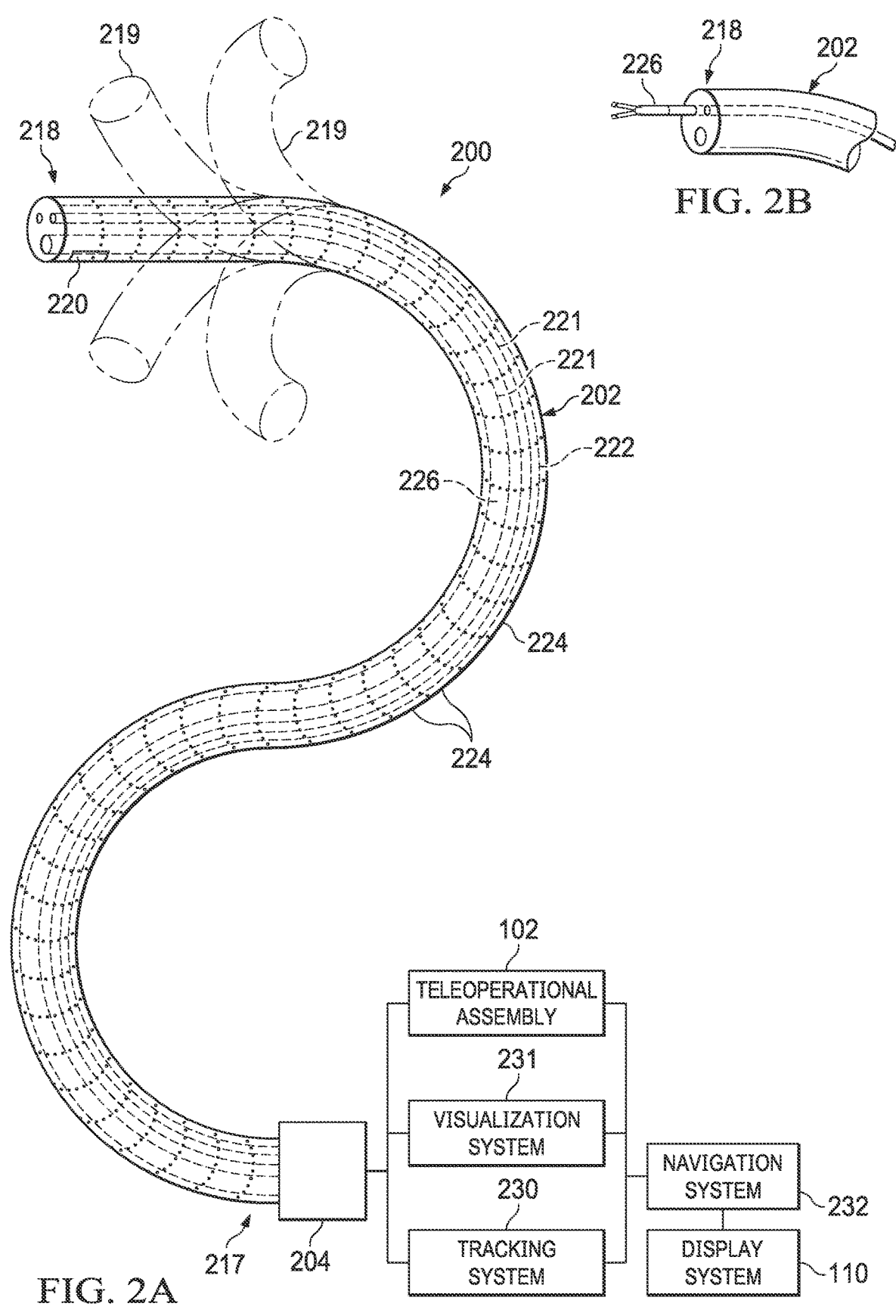
FIG. 2A illustrates an instrument system utilizing aspects of the present disclosure.
FIG. 2B illustrates a distal portion of the instrument system of FIG. 2A with an extended example of an instrument in accordance with the present disclosure.

FIG. 2A illustrates a medical instrument system 200 in accordance aspects of the present disclosure, which may be used as or in the medical instrument system 104 in an image-guided medical procedure performed with teleoperational system 100. Alternatively, the medical instrument system 200 may be used for non-teleoperational exploratory procedures or in procedures involving traditional manually operated medical instruments, such as endoscopy.

The instrument system 200 includes a flexible steerable body 202 coupled to a housing 204. The flexible steerable body 202 has a proximal end 217 and a distal end or tip portion 218. In various embodiments, the flexible steerable body 202 has a size and shape to reach a target anatomy, such as, for example, a 4 mm to 25 mm diameter. Other flexible steerable body outer diameters may be larger or smaller. The instrument system 200 may optionally include one or more shape sensors 222 for determining the position, orientation, speed, velocity, pose, shape, or other physical characteristic of the flexible steerable body tip at distal end 218, of one or more segments 224 along the flexible steerable body 202, and/or along at least a portion of an instrument positionable within lumens or channels 221 of the flexible steerable body 202 (for example, instruments 226 described in further detail below). The entire length of the flexible steerable body 202, between the distal end 218 and the proximal end 217, may be effectively divided into the segments 224. If the instrument system 200 is a medical instrument system of a teleoperational system 100, such as medical instrument system 104, the shape sensor 222 may be a component of the sensor system 108. If the instrument system 200 is manually operated or otherwise used for non-teleoperational procedures, the shape sensor 222 may be coupled to a tracking system 230 that interrogates the shape sensor 222 and processes the received shape data. In some embodiments, optionally, the flexible steerable body 202 may include one or more shape sensors 222. Additionally or alternatively, instruments 226 that are coupled to the flexible steerable body 202 or positioned within lumens 221 of the flexible steerable body 202 may optionally include shape sensors 222.

The medical instrument system 200 (e.g., the steerable body 202 and/or instruments 226) may, optionally, include one or more position sensor systems 220 and/or shape sensors 222 which may be provided within or mounted externally to a flexible steerable body 202 or instrument 226. Various systems and methods for monitoring shape and relative positions of instruments are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"); U.S. patent application Ser. No. 13/107,562 (filed May 13, 2011) (disclosing, "Medical System Providing Dynamic Registration of a Model of an Anatomic Structure for Image-Guided Surgery); U.S. Pat. No. 6,380,732 (filed Aug. 11, 1999) (disclosing "Six-Degree of Freedom Tracking System Having a Passive Transponder on the Object Being Tracked"); and U.S. Provisional Patent Application 63/240,471 (filed on Sep. 3, 2021) (disclosing "Ultrasound Elongate Instrument Systems and Methods"), which are all incorporated by reference herein in their entireties. A tracking system 230 may include one or more position sensor systems 220 and one or more shape sensors 222 for determining the position, orientation, speed, pose, and/or shape of the instruments. The tracking system 230 may be implemented as hardware, firmware, software or a combination thereof which interact with or are otherwise executed by one or more computer processors, which may include the processors of a control system 112.

Figure 2C:
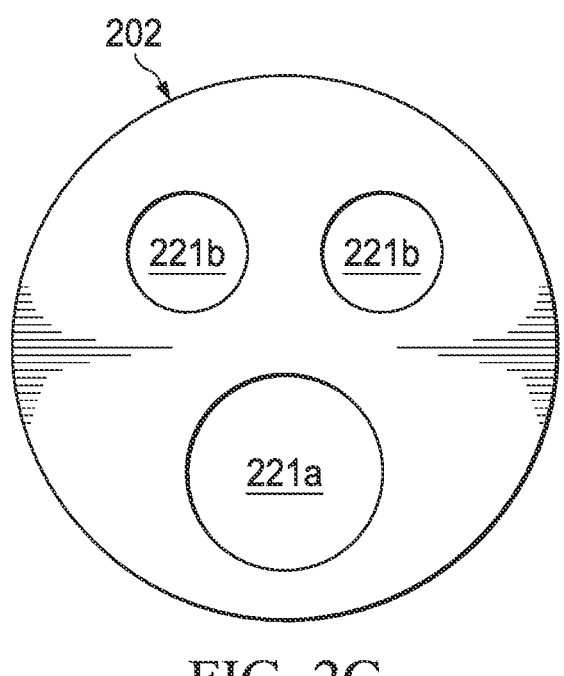
FIG. 2C illustrates a distal end of the flexible steerable device of the instrument system of FIG. 2A.

The flexible steerable body 202 includes one or more lumens 221 sized and shaped to receive one or more medical instruments 226. Medical instruments may include, for example, image capture devices (e.g., an endoscope, such as a monoscopic or stereoscopic endoscope), electrosurgical devices, biopsy instruments, laser ablation fibers, or other surgical, diagnostic, or therapeutic tools. Medical instruments may include end effectors having one or more working members such as a scalpel, a blunt blade, an optical fiber, or an electrode. Other end effectors may include, for example, forceps, grippers, scissors, clip appliers, etc. Examples of electrically activated end effectors include electrosurgical electrodes, transducers, sensors, and the like. One or more of the lumens 221 may have a diameter of approximately 3 mm to 20 mm, for example. In one example, a lumen 221b configured to receive an approximately 5 mm instrument may have a diameter of approximately 6 mm. A lumen 221a may have a larger diameter to receive a larger instrument such as an image capture device. For example, as shown in FIG. 2C, the flexible steerable body 202 may include a lumen 221a sized to receive a larger instrument such as an image capture device, and two lumens 221b each sized to receive a flexible instrument 226. However, other embodiments may include more or fewer lumens 221a and/or 221b (such as one, two, three, four, or more lumens 221a, 221b). The lumens 221a, 221b may have different sizes relative to each other, or two or more of the lumens 221a, 221b may have the same size. In some embodiments, the larger lumen 221a may be positioned below the smaller lumens 221b as in FIG. 2C, or the larger lumen 221a may be positioned above the smaller lumens 221b, or the larger lumen 221a may be positioned along a common horizontal plane with one or more of the smaller lumens 221b.

In various embodiments, one or more of the medical instruments 226 may be or include an image capture device that includes a distal portion with a stereoscopic or monoscopic camera that are processed by a visualization system 231 for display. The image capture device may include a cable coupled to the camera for transmitting the captured image data. Alternatively, the image capture device may be a fiber-optic bundle, such as a fiberscope, that couples to the visualization system. The image capture device may be single or multi-spectral, for example capturing image data in one or more of the visible, infrared, or ultraviolet spectrums.

Figure 2D:
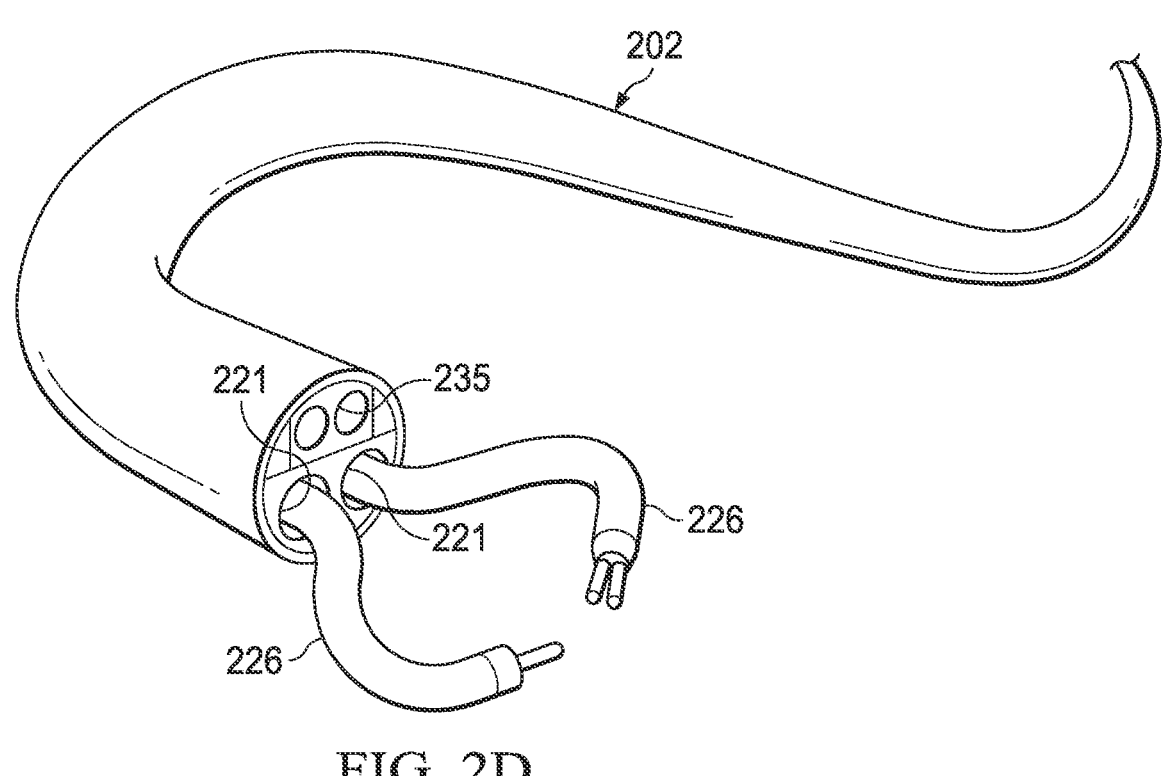
FIG. 2D illustrates a distal portion of an instrument system utilizing aspects of the present disclosure.

In some embodiments, a flexible steerable body 202 may include an image capture device 235, such as a stereoscopic camera, disposed at or near the distal end 218, as illustrated in FIG. 2D, for capturing images (including video images). A plurality of lumens 221 extending through the flexible steerable body 202 may provide access for a plurality of instruments 226 to access a surgical site within a field of view of the image capture device. For example, as shown in FIG. 2D, the flexible steerable body 202 may include an image capture device 235, and two lumens 221 each receiving a flexible instrument 226. However, other embodiments may include more or fewer lumens 221 (such as one, two, three, four, or more lumens). The lumens 221 may have different sizes relative to each other, or two or more of the lumens 221 may have the same size. In some embodiments, the image capture device 235 may be positioned below the lumens 221, or the image capture device 235 may be positioned above the lumens 221, or the image capture device 235 may be positioned along a common horizontal plane with one or more of the lumens 221.

The medical instrument 226 may house cables, linkages, or other actuation controls (not shown) that extend between the proximal and distal ends of the instrument to controllably bend the distal end of the instrument. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

The flexible steerable body 202 may also houses cables, linkages, or other steering controls (not shown) that extend between the housing 204 and the distal end 218 to controllably bend the distal end 218 as shown, for example, by the broken dashed line depictions 219 of the distal end of the flexible steerable body 202. Flexible steerable bodies, such as catheters, are described in detail in U.S. patent application Ser. No. 13/274,208 (filed Oct. 14, 2011) (disclosing "Catheter with Removable Vision Probe"), which is incorporated by reference herein in its entirety. In embodiments in which the instrument system 200 is actuated by a teleoperational assembly such as teleoperational manipulator assembly 102, the housing 204 may include drive inputs that removably couple to and receive power from motorized drive elements of the teleoperational assembly. In embodiments in which the instrument system 200 is manually operated in whole or in part, the housing 204 may include gripping features, manual actuators, or other components for manually controlling the motion of the instrument system 200. The instrument system 200 may be steerable or, alternatively, the system may be non-steerable with no integrated mechanism for operator control of the instrument bending. Also or alternatively, one or more lumens, through which medical instruments can be deployed and used at a target surgical location, are defined in the walls of the flexible steerable body 202.

In various embodiments, the medical instrument system 200 may include a flexible instrument suited for navigation and treatment of tissues, via natural or surgically created connected passageways, in any of a variety of anatomic systems, including the colon, the intestines, the kidneys, the brain, the heart, the circulatory system, pulmonary system, the stomach, other gastrointestinal passageways, and the like.

In the embodiment of FIG. 2A, the instrument system 200 is teleoperated within the teleoperational system 100. In an alternative embodiment, the teleoperational manipulator assembly 102 may be replaced by direct operator control. In the direct operation alternative, various handles and operator interfaces may be included for hand-held operation of the instrument.

As shown in greater detail in FIG. 2B, medical instruments (such as medical instrument 226) for such procedures as surgery, biopsy, ablation, illumination, irrigation, or suction can be deployed through one or more lumens of the flexible steerable body 202 and used at a target location within the anatomy. The medical instrument 226 may be used with an image capture device (e.g., an endoscope) also within the flexible steerable body 202. Alternatively, the medical instrument 226 may itself be the image capture device. The medical instrument 226 may be advanced from the opening of a lumen 221 to perform a procedure and then retracted back into the lumen when the procedure is complete. In some embodiments, optionally, the medical instrument 226 may be removed from the proximal end 217 of the flexible steerable body 202 or from another optional instrument port (not shown) along the flexible steerable body.

Figure 3:
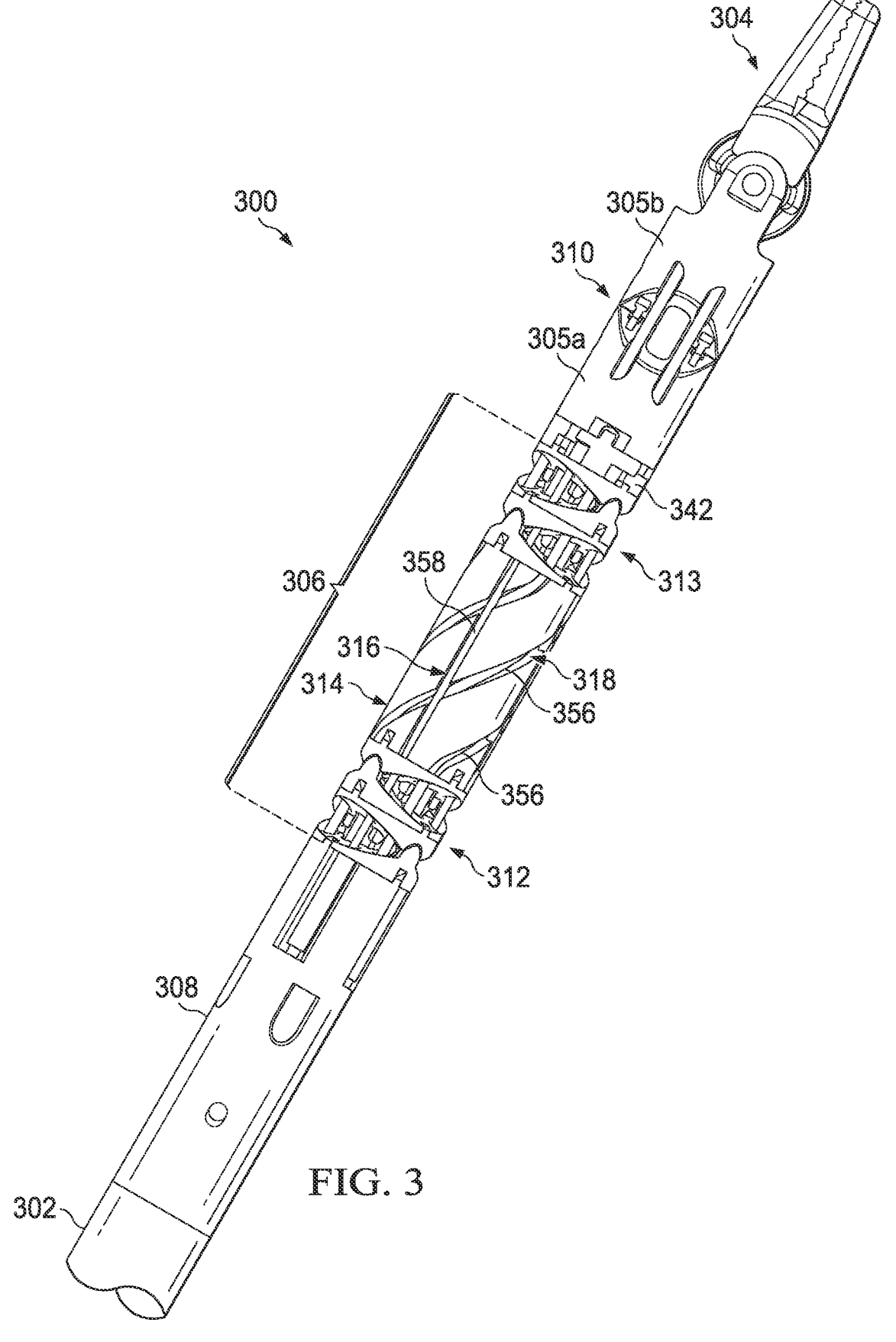
FIG. 3 illustrates a distal portion of an instrument in accordance with the present disclosure.

FIG. 3 illustrates a distal portion of an instrument 300 which may be an example of medical instrument 226 as shown in FIGS. 2B and 2D, having a counter-pivoting mechanism 306. Individual components of the counter-pivoting mechanism 306 are discussed in relation to FIGS. 4-7B below. It should be appreciated that instrument 300 may be extended from a guide device, such as flexible steerable body 202, may be used independently without a guide device, or may itself be a guide device to guide tools to a target site. Although described in the context of a medical instrument used in a teleoperational system, it should be appreciated that the disclosure herein contemplates use of a counter-pivoting mechanism in non-medical instruments (e.g., mechanical repair or manufacturing applications) and in non-teleoperational (e.g., hand-held) instruments.

The instrument 300 may include an elongate shaft 302, an end effector 304, and the counter-pivoting mechanism 306 disposed between the elongate shaft and end effector. An adapter 308 may secure the counter-pivoting mechanism 306 to the elongate shaft 302, although it should be appreciated that in other examples the counter-pivoting mechanism 306 may comprise a portion of the elongate shaft such that the adapter 308 may be omitted. A wrist assembly 310, which may include a plurality of links such as proximal link 305a and distal link 305b, may be disposed between the counter-pivoting mechanism 306 and the end effector 304. Although shown in the illustrated example as a gripper having two jaws, the end effector 304 may be any suitable tool including, but not limited to, an ablation tool, a biopsy tool, an image capture device, a therapeutic tool, etc. Although not shown in order to avoid obscuring the features described herein, a flexible outer sheath or braid may extend over some or all of the elongate shaft 302, adapter 308, counter-pivoting mechanism 306, wrist assembly 310, and/or end effector 304. The flexible outer sheath may prevent fluids, tissue, or other debris from entering the instrument 300.

The counter-pivoting mechanism 306 provides counter-pivoting motion between components positioned on opposite ends of the mechanism 306. In particular, one or more joints in a first portion of the counter-pivoting mechanism 306 are caused to pivot in a first direction as a result of one or more other joints in a second portion of the counter-pivoting mechanism 306 being bent in a second direction which is opposite, or otherwise different than, the first direction. In some embodiments, the counter-pivoting mechanism 306 allows bending or pivoting of a distal portion of the instrument 300 without changing an orientation of the distal portion of the instrument relative to a proximal portion of the instrument. That is, the counter-pivoting mechanism 306 is configured to maintain a portion of the instrument 300 distal of the counter-pivoting mechanism (e.g., the end effector 304 and/or the wrist assembly 310) in a parallel orientation to a portion of the instrument proximal of the counter-pivoting mechanism (e.g., the elongate shaft 302 or adapter 308) during bending of the counter-pivoting mechanism to translate the distal portion with respect to the proximal portion without a change in orientation. The counter-pivoting mechanism 306 allows multiple instruments (such as instrument 300) to be extended out from the distal end of a guide device (such as flexible steerable body 202) and splayed apart, as shown for example in FIG. 2D, to provide increased working space between the instruments for range of manipulation without interference and a wider range of approach angles to a target tissue. The orientation of the wrists being maintained with the orientation of the shafts, by the counter-pivoting mechanisms, as the end effectors are splayed apart allows the wrists to retain their range of manipulation without having to compensate for a change in orientation that may otherwise be caused by splaying the instruments apart. In the illustrated example, the distal portion of the instrument may be a proximal link 305a of the wrist assembly 310 and the proximal portion may be the adapter 308 such that as bending occurs in the counter-pivoting mechanism 306, the proximal link 305a of the wrist assembly 310 is maintained in a parallel, or otherwise constant, orientation with respect to the adapter 308. However, it should be appreciated that a counter-pivoting mechanism 306 may be configured to maintain a constant orientation between other portions or components of an instrument which are disposed on opposing sides of the counter-pivoting mechanism. Further, in some embodiments, the counter-pivoting mechanism 306 may provide counter-pivoting motion whereby a portion of the instrument 300 distal to the counter-pivoting mechanism 306 pivots in an opposite direction to a portion proximal of the counter-pivoting mechanism 306 without maintaining a parallel or constant orientation. For example, the counter-pivoting motion may deviate from a parallel orientation, such that the distal portion has some amount of change in orientation relative to the proximal portion.

The illustrated counter-pivoting mechanism 306 may include an elongate tube 314, with control cables 356 and constraint cables 358 that extend through the elongate tube, and a proximal joint assembly 312 and a distal joint assembly 313 formed by links on either end of the elongate tube. Channels or grooves 316, 318 formed in the elongate tube may receive the cables 356, 358. The control cables 356 are actuated to articulate the joint assemblies 312, 313 to translate the wrist assembly 310 and/or end effector 304 in a desired direction with respect to the elongate shaft 302. The constraint cables 358 cause opposed pivoting movements in the joint assemblies 312, 313 to maintain an orientation of the wrist assembly 310 and/or end effector 304 during such translation caused by the control cables 356. As described further below, the grooves 316, 318 into which the cables are disposed may be formed in an outer circumferential surface of the elongate tube 314, which may aid in assembly and manufacturing of the device.

Figure 5A:
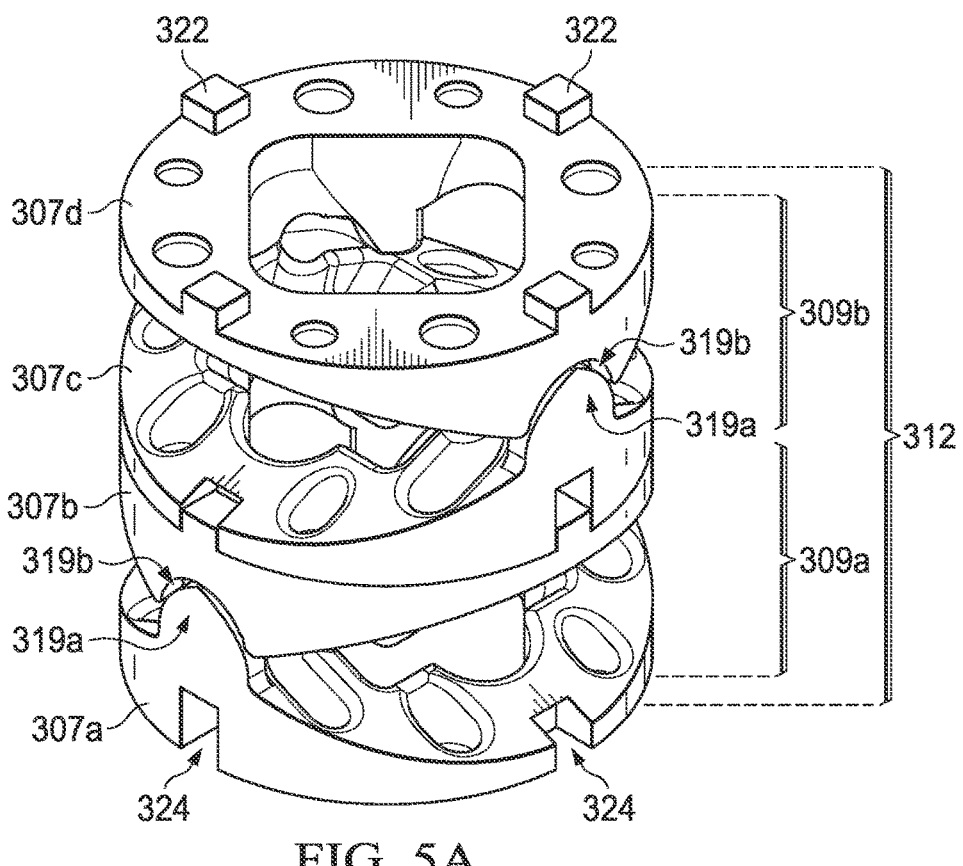
FIG. 5A illustrates a plurality of counter-pivoting mechanism joints formed by links in accordance with the present disclosure.
Figure 8A:
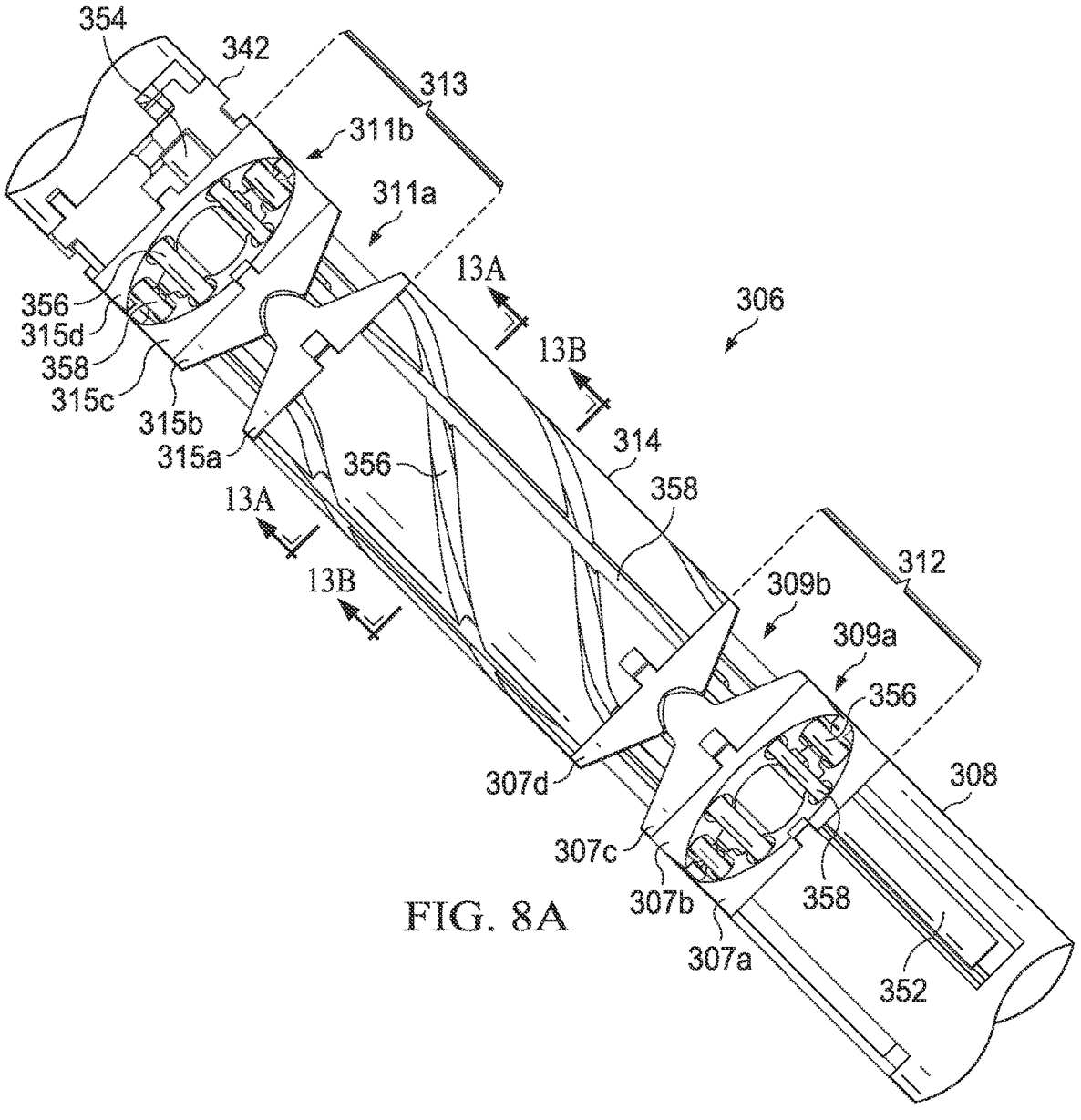
FIGS. 8A-8B illustrate a counter-pivoting mechanism in accordance with the present disclosure in a straight and a bent configuration, respectively.
Figure 8B:
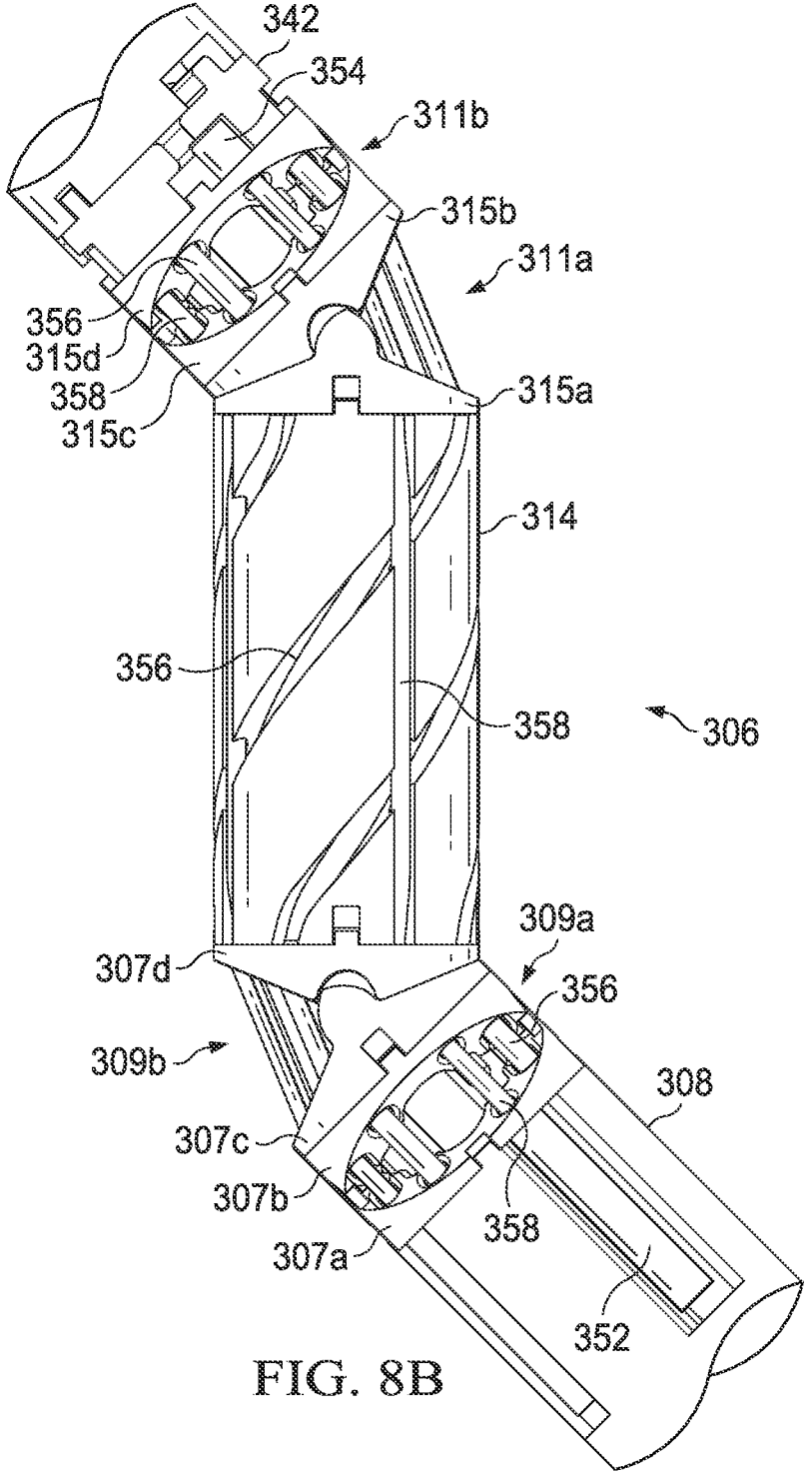

FIGS. 5A and 8A-8B provide further illustration of the arrangement of links in the proximal joint assembly 312 and distal joint assembly 313. As discussed further below, the constraint cables 358 may extend axially through the length of the counter-pivoting mechanism 306 in a first plurality of channels or grooves 316 formed in the elongate tube 314 (e.g., in a configuration aligned or parallel with a longitudinal axis of the elongate tube 314). The constraint cables 358 may terminate proximally at the adapter 308 and may terminate distally at an anchor link 342 disposed distally of the joints 313. In some examples, the anchor link 342 may be omitted and the constraint cables 358 may terminate distally at distal-most link of the distal joint assembly 313. Due to the constraint cables 358 having a fixed length and being fixedly secured at a distal end and a proximal end of the counter-pivoting mechanism 306, opposing pairs of constraint cables 358 maintain parallel motion of the counter-pivoting mechanism as the mechanism is actuated by the control cables 356. However, in other embodiments, the constraint cables 358 provide counter-pivoting motion that deviates from a parallel orientation.

The control cables 356 may extend through coil pipes (not shown) extending within the elongate shaft 302 from a proximal portion of the elongate shaft. The coil pipes may terminate prior to the counter-pivoting mechanism 306, for example at a proximal-most link 307a (FIG. 5A) of the counter-pivoting mechanism, at the adapter 308, or proximally thereof. In some embodiments, optionally, coil pipes may be used to receive an axial compressive load when a cable disposed within a respective coil pipe is pulled, thereby isolating movement caused by pulling on the cable to components that are distal of the coil pipe while preventing bending along the length of the coil pipe, for example in a flexible elongate shaft 302. The coil pipes may be similar to those described in as described in U.S. Pat. Pub. No. US 2016/0067450 (filed Sep. 3, 2015) (disclosing "Flexible Instrument with Nested Conduits") which is incorporated by reference herein in its entirety. In other examples, the elongate shaft 302 may be rigid and, accordingly, coil pipes may be omitted as the rigidity of the elongate shaft 302 itself may prevent bending and isolate movement to the components distal of the elongate shaft 302.

The control cables 356 may extend distally from the shaft continue through the counter-pivoting mechanism 306 in a second plurality of grooves or channels 318 formed in the elongate tube 314. The channels 318 may be positioned helically in the elongate tube 314 such that the control cables 356 may wrap helically around the elongate tube 314 within the channels 318. For example, referring to FIG. 3, a control cable 356 entering the elongate tube 314 on the left side at the proximal end may exit the elongate tube on the right side at the distal end at a radial position approximately 180° (e.g., 150°-210°) from where the control cable 356 enters the elongate tube. The control cables 356 may terminate at and may be fixed to a distal portion of the counter-pivoting mechanism 306 or distally thereof. In the illustrated example, the control cables 356 may terminate at the anchor link 342 distal of the distal joints 312. In some examples, crimps or sleeves may be attached to the ends of the control cables to anchor the control cables in a manner similar to the constraint cables.

Generally, a length (or the proximal and distal limits) of the counter-pivoting mechanism 306 may be defined by the anchor points at which the ends of the constraint cables 358 are fixed or secured to the instrument 300. In the illustrated example, the counter-pivoting mechanism 306 may begin at the proximal side of the most proximal link 307a of the proximal joint assembly 312 near the adapter 308 and may terminate at the distal side of the most distal link 315d of the distal joint assembly 313 near the wrist assembly 310 (see FIG. 8A). Further, although shown with two proximal joints 309a, 309b and two distal joints 311a, 311b (FIG. 8A), a counter-pivoting mechanism 306 may include any number of joints on each end of the elongate tube 314. By utilizing two proximal joints 309 and two distal joints 311 (which may each comprise two links 307, 315 or which may share a common link) on each end of the counter-pivoting mechanism 306, the two joints on each end may be configured to pivot in orthogonal directions to provide movement in both a pitch direction and a yaw direction. In some examples, the adapter 308, the anchor link 342, and/or the wrist assembly 310 may be considered part of the counter-pivoting mechanism 306.

Figures 4, 6:
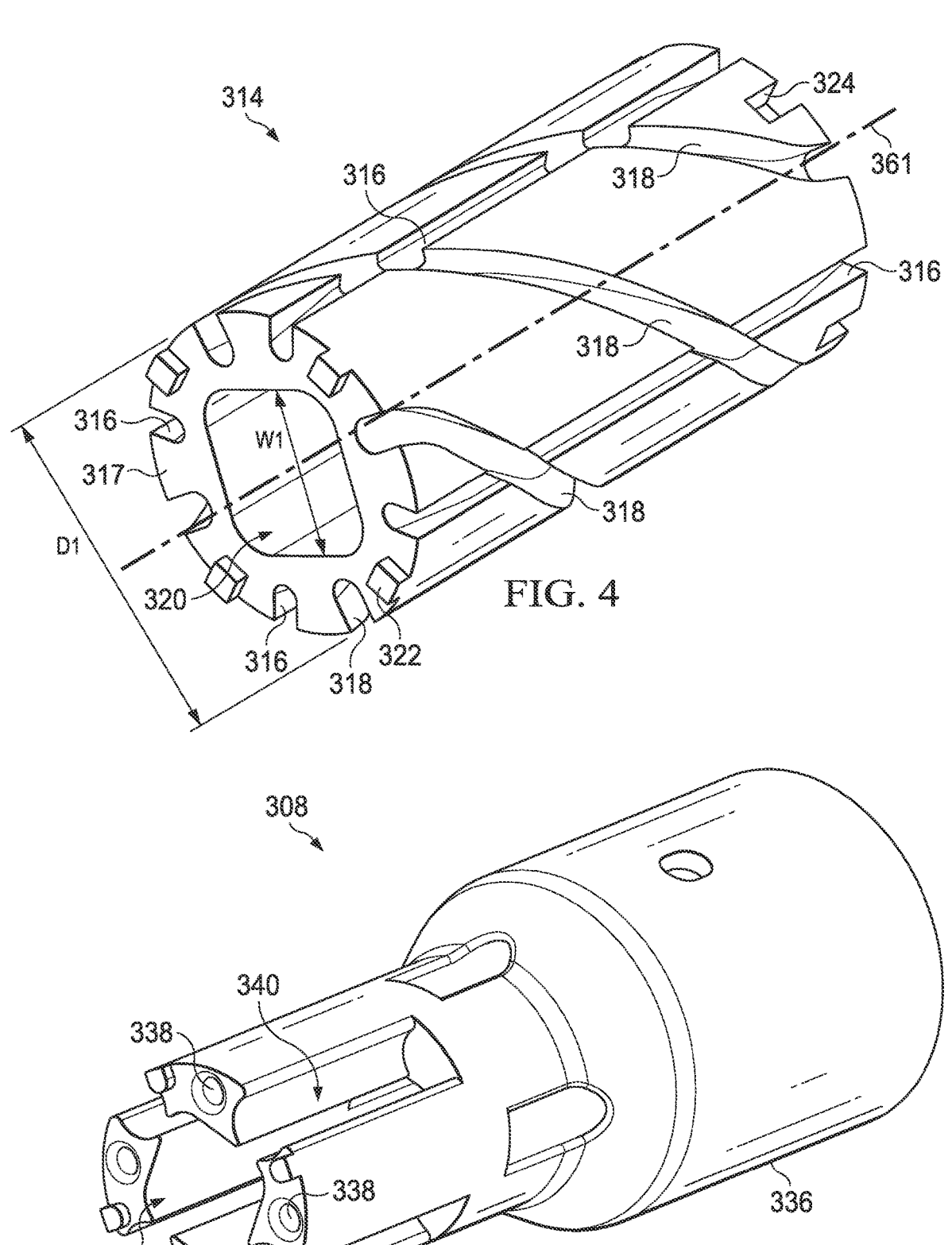
FIG. 4 illustrates an elongated tube of a counter-pivoting mechanism in accordance with the present disclosure.
FIG. 6 illustrates an adapter for connecting a counter-pivoting mechanism to an elongate shaft of an instrument in accordance with the present disclosure.

FIG. 4 illustrates an example of an elongate tube 314 as used in the counter-pivoting mechanism 306 of FIG. 3. The elongate tube 314 comprises a wall 317 formed around a central lumen 320 extending along a longitudinal axis 361 of the elongate tube. An outer diameter D1 of the elongate tube 314 may be approximately 2 mm to 20 mm. In one example, the outer diameter of the elongate tube 314 is approximately 5 mm, such as 4 mm or 6 mm. The central lumen 320 is illustrated has having a substantially square cross-section but may be circular or any other suitable shape. The central lumen 320 may have a width or diameter W1 that is approximately 1 mm-10 mm. In one example for an elongate tube 314 having an outer diameter of approximately 5 mm, the maximum dimension W1 across the central lumen 320 may be approximately 2.8 mm, such as 2.5 mm or 3.0 mm.

On an outer circumferential surface of the elongate tube 314, a plurality of first grooves 316 and a plurality of second grooves 318 are formed. The first grooves 316 are configured to receive a plurality of constraint cables 358 and the second grooves 318 are configured to receive a plurality of control cables 356. The first grooves 316 are substantially linear along the length of the elongate tube 314 (e.g., the first grooves 316 extend along or parallel to the longitudinal axis 361 of the elongate tube 314). The second grooves 318 wrap helically or spirally around the elongate tube. The second grooves 318 are formed deeper into the wall than the first grooves 316. In this manner, the constraint cables 358 may pass over the control cables 356 as the constraint cables 358 are disposed radially outward from the control cables 356 with respect to the longitudinal axis 361, as shown for example in FIGS. 13A-13B. This arrangement may provide for the constraint cables 358 to exert a radially inward force to assist in retaining the control cables 356 in their respective second grooves 318. It should be appreciated that in other examples, the first grooves 316 may be formed deeper into the wall of the elongate tube 314 and the second grooves 318 may be formed shallower such that the control cables 356 are disposed radially outward from the constraint cables 358. In some examples, the first grooves 316 for receiving the constraint cables 358 may also helically wrap around the elongate tube 314 in the same or opposite direction as the second grooves 318, or both the first and second grooves 316, 318 may extend substantially linearly along the elongate tube 314. In some examples, the control cables 356 may be wrapped on the outside of the tube 314 (e.g., in straight or helical grooves 318) and the constraint cables 358 may be routed through the central lumen 320 or through other lumens in the wall of the tube 314. In some examples, four first grooves 316 and four second grooves 318 are formed in the elongate tube 314. The first grooves 316 may be circumferentially spaced 90° apart. The second grooves may also be circumferentially spaced 90° apart. At the distal and proximal ends of the elongate tube 314, each first groove 316 may be disposed between two adjacent second grooves 318. In some examples, more or fewer than four first and/or second grooves may be used. In some examples, three control cables 356 and three second groves 318 may be used, each being spaced circumferentially by approximately 120°. In some examples, three constraint cables 358 and three first grooves 316 may be used. The first and/or second grooves may be equally spaced around the circumference of the elongate tube 314 or may be spaced unevenly.

The length of the elongate tube 314 and pitch angle of the plurality of second grooves 318 in the illustrated example of FIG. 4 provide for each second groove 318 to terminate at the distal end of the elongate tube at a radial position approximately 180° from its respective radial position at the proximal end of the elongate tube. However, the elongate tube 314 may be shorter or longer and the pitch angle of the second grooves 318 may be steeper or shallower depending on preferred properties of a particular design application. In this regard, the second grooves 318 may wrap less than or greater than 180° along the length of the elongate tube 314, for example 90° or less or 360° or more.

Figure 5B:
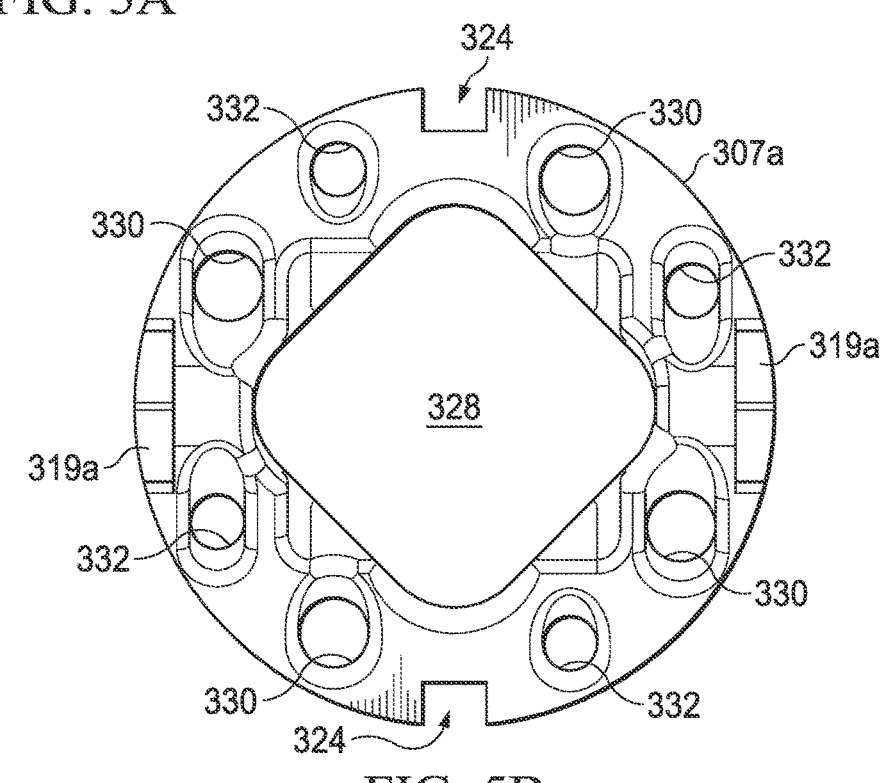
FIG. 5B illustrates a link as shown in FIG. 5A.

One end surface of the elongate tube 314 includes a plurality of protrusions 322 and the opposing end surface comprises a plurality of recesses 324 extending therefrom, as illustrated in FIG. 4. The protrusions 322 and recesses 324 may be configured to matingly engage corresponding protrusions 322 and recesses 324 on components adject to the elongate tube 314, for example, a distal or a proximal pivot link 326 as shown in FIGS. 5A-5B. Engagement of corresponding pairs of protrusions 322 and recesses 324 may resist translation and rotation of adjacent components.

Actuation (e.g., pulling or pushing) of control cables 356 causes bending of the counter-pivoting mechanism 306 and a corresponding translation of the components distal to the counter-pivoting mechanism (namely, the end effector 304 and wrist assembly 310), while the constraint cables 358 retain a link pair 307a, 315d in a parallel arrangement during such translation.

As compared to parallel motion mechanisms that include two coaxial tubes with cables routed between an inner tube and an outer tube, the design of counter-pivoting mechanism 306 may provide several desirable features. For example, the counter-pivoting mechanism 306 may eliminate one of the two tubes in a parallel motion mechanism, thereby allowing the outer diameter of the counter-pivoting mechanism to be reduced from 6 mm or greater to less than 5 mm while also allowing the inner diameter or cross-sectional area of the central lumen 320 to be increased, thereby providing a greater inner diameter to outer diameter (or central lumen cross-sectional area to total cross-sectional area) ratio. The increased area of the central lumen 320 may permit wrist and/or end effector cables to be routed through coil pipes within the central lumen 320 which helps isolate wrist actuation loads from affecting the alignment or orientation of the counter-pivoting mechanism 306. The central lumen 320 may additionally house electrical wires (e.g., supplying power to an electrocautery tool), a shape sensor, grip controls (push-pull or pull-pull), and/or additional coil pipes housing these components. In some examples, a compact arrangement of a plurality of components extending through the central lumen 320, such as electrical wires, a shape sensor, a grip control, etc., may behave similar to a coil pipe to isolate actuation loads from the wrist and/or end effector cables without using coil pipes. The decreased outer diameter of the elongate tube 314 may increase the suitability of the instrument 300 for endoluminal use in tight anatomical spaces in which the instrument may be inserted through a working channel of a flexible steerable body, for example, during upper or lower gastrointestinal procedures.

Further, the proposed design may provide for simplified manufacturing and assembly of the counter-pivoting mechanism 306. For example, routing the control and/or constraint cables within an outer surface of the wall of the elongate tube 314 may eliminate the need for a separate internal tube. The cables can be quickly inserted into the grooves 316, 318 in a radial direction from outside the elongate tube which may eliminate the difficult task of feeding the cables longitudinally through narrow openings in the counter-pivoting mechanism as compared to existing devices. The ability to externally view the routing of cables after installation may also allow for visual confirmation that the cables are routed appropriately and not incorrectly crossed.

FIG. 5A illustrates an example of a proximal joint assembly 312 which includes a pair of joints 309a, 309b. The first joint 309a comprises a first link 307a and a second link 307b. The second joint 309b comprises a third link 307c and a fourth link 307d. The first link 307a and the third link 307c may be identical or may each have unique features. Similarly, the second link 307b and the fourth link 307d may be identical or may each have unique features. In some examples, the first joint 309a and the second joint 309b may each include a common central link rather than having two discrete pairs of links.

Each of the first link 307a and the third link 307c includes a first mating feature 319a and each of the second link 307b and the fourth link 307d includes a corresponding second mating feature 319b such that each joint pivots about an axis of rotation extending through the first and second mating features. Various mating feature arrangements are described in U.S. Pat. No. 6,817,974 (filed Jun. 28, 2002) (disclosing "Surgical Tool Having Positively Positionable Tendon-Actuated Multi-Disk Wrist Joint"), which is incorporated herein by reference in its entirety. The links 307 may be secured together with any suitable first and second mating features 319a, 319b such as a pair of grooves and corresponding protrusions as shown, with a hinge pin extending along the axis of rotation, with a radial section of interleaved gear teeth, or with any other suitable fixation mechanism. As can be appreciated from the arrangement shown in FIG. 5A, the axis of rotation of the first joint 309a is orthogonal to the axis of rotation of the second joint 309b. In this regard, the two joints 309a, 309b facilitate pivoting movement of the instrument 300 in both a yaw direction and a pitch direction, as well as any combination thereof. A distal joint assembly 313 may be identical to the proximal joint assembly 312 shown in FIG. 5A or may have unique features. For example, a counter-pivoting mechanism 306 may have more proximal joints 309 than distal joints 311 or may have more distal joints 311 than proximal joints 309. The distal links 315 of a distal joint assembly 313 may have different mating features than the proximal links 307 of a proximal joint assembly 312.

FIG. 5B illustrates an example of first link 307a having a central lumen 328, a plurality of control cable lumens 330, and a plurality of constraint cable lumens 332. A first mating feature 319a comprises a pair of protrusions configured to pivotally engage corresponding recesses on an adjacent link 307. A plurality of recesses 324 are provided for mating engagement with protrusions 322 of an adjacent link 307, adapter 308, or elongate tube 314. The other links 307 of the proximal joint assembly 312 and the links 315 of the distal joint assembly 313 may have similar or related features.

FIG. 6 illustrates another example of an adapter 308 which may be similar to the adapter illustrated in FIG. 3. A flange 336 at the proximal end of the adapter 308 may be sized to receive and couple to a distal end of the elongate shaft 302 by any suitable mechanism (fasteners, adhesives, etc.). A distal portion of the adapter 308 includes a plurality of anchor recesses 340 each configured to receive a proximal anchor 352 of a corresponding constraint cable. A plurality of control cable lumens 338 extend between adjacent anchor recesses 340. The control cables 356 may extend through coil pipes in the elongate shaft 302 of the instrument 300, with the coil pipes terminating within the adapter 308. The control cables 356 then extend through the control cable lumens 338 and into the proximal joint assembly 312 of the counter-pivoting mechanism 306. A distal end surface of the adapter 308 includes a plurality of protrusions 322 configured to matingly engage corresponding recesses of an adjacent link such as first link 307a. Alternatively, the adapter 308 may comprise recesses configured to matingly engage corresponding protrusions on an adjacent proximal link 307. In some examples, the adapter 308 may be welded to an adjacent proximal link 307.

Figure 7A:
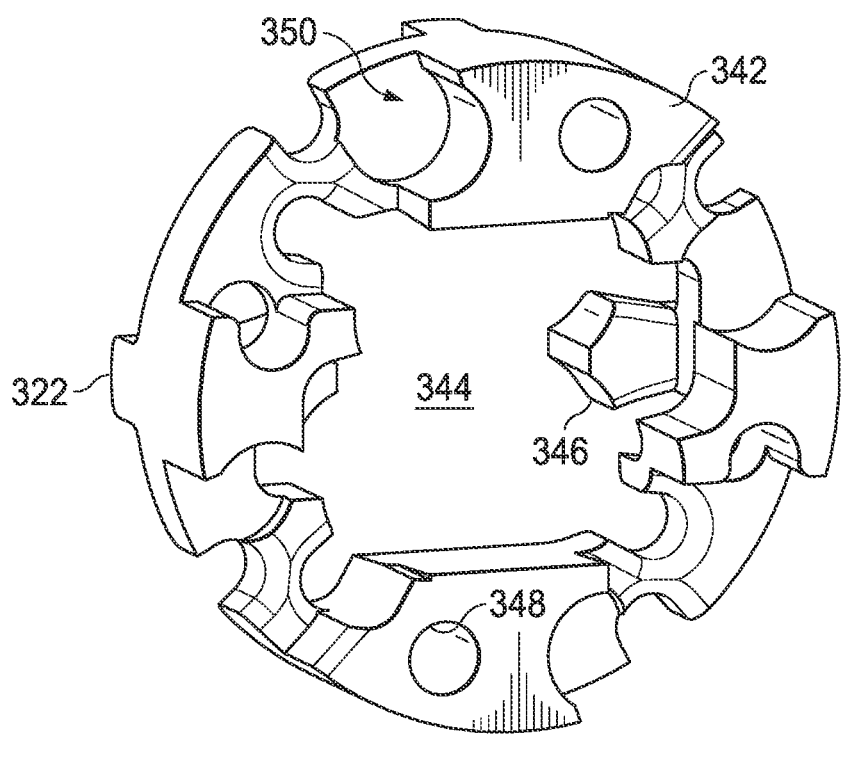
FIGS. 7A-7B illustrate an anchor link of a counter-pivoting mechanism in accordance with the present disclosure.
Figure 7B:
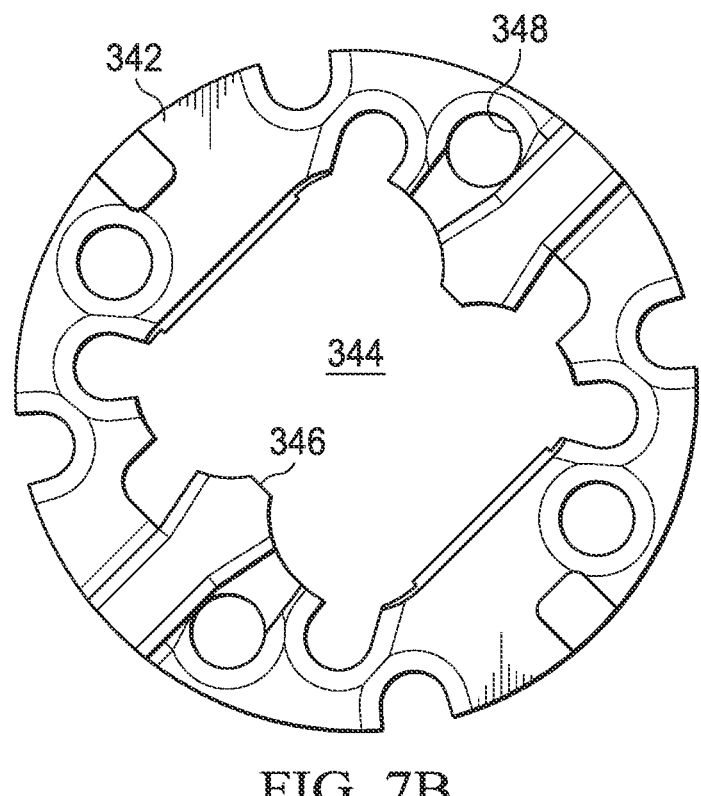

FIGS. 7A-7B illustrate a proximal side and a distal side, respectively, of an anchor link 342 which is configured to be positioned between the distal joint assembly 313 and the wrist assembly 310, as shown in FIG. 3. Similar to the adapter 308, the links 307, 315, and the elongate tube 314, the anchor link 342 also includes a central lumen 344 which is aligned with the central lumens 320, 328, and 334 in the counter-pivoting mechanism 306 to house pull wires, control cables, and other mechanisms extending from the elongate shaft 302 to the wrist assembly 310 and/or end effector 304. The anchor link 342 includes a plurality of supports 346 which extend into the central lumen 344. The supports 346 may serve as a cleat or post for anchoring the control cables 356. In some examples, a pair of control cables 356 may comprise a single cable that extends from the proximal end of the elongate shaft 302 to the anchor link 342, is tied off or looped around one of the supports 346 and/or other features of the anchor link 342, and then extends back through the elongate shaft 302. With the central portion of the cable fixed to the anchor link 342, the single cable may behave as two separate control cables 356. In the illustrated example, the supports 346 include curved surfaces configured to accommodate a correspondingly shaped outer surface of coil pipes through which end effector and/or wrist assembly control cables extend. Although it will be appreciated that the supports 346 may be omitted in some examples as the control cables 356 may be anchored in another manner (e.g., crimps), when included, they may help to retain the coil pipes in their respective corner of the central lumen 344 (as well as central lumens 320, 328, and 334), thereby leaving an opening in the center of the central lumen 344 which may accommodate electrical wires, push or pull rods for an end effector, tools (e.g., a biopsy needle), etc.

The proximal side of the anchor link 342 includes a plurality of anchor recesses 350 configured to receive a distal anchor 354 (e.g., a crimp or sleeve) of a respective constraint cable 358. A plurality of control cable lumens 348 extend through the anchor link 342 such that the control cables 356 pass through the control cable lumens 348 and are tied to the anchor link. It will be appreciated that in other examples, the control cables 356 and/or constraint cables 358 may terminate distally or proximally of the anchor link 342 and may be anchored in any suitable manner. In some examples, the anchor link 342 may be omitted and the control cables 356 and constraint cables 358 may be anchored to another component such as a link of the distal joint assembly 313 or to an end effector component such as a proximal wrist link.

FIGS. 8A-8B illustrate bending of the counter-pivoting mechanism 306 from a top view according to some embodiments. In FIG. 8A, the counter-pivoting mechanism 306 is in a neutral or straight configuration in which all of the joints 309a-b, 311a-b are linearly aligned with the longitudinal axis 361 of the elongate tube 314. In FIG. 8B, the control cables 356 have been actuated (e.g., by actuators of the teleoperational manipulator assembly 102) to bend joint 311a to the left in a first direction (e.g., a yaw direction). This pivoting movement causes tension in the constraint cables, which are not directly controlled by actuators. The tension in the constraint cables exerts a reciprocal actuation force on the joint 309b bending it to the right in a direction opposite to the first direction by an equal amount, maintaining a parallel orientation between proximal link 307a and distal link 315d. In this regard the anchor link 342 and other components distal thereof are retained in the same orientation with respect to the adapter 308 and/or elongate shaft 302 as they had before actuation of the counter-pivoting mechanism 306. That is, absent any separate actuation of the wrist assembly 310 or end effector 304, the components of the wrist assembly 310 and end effector 304 will retain the same orientation with respect to the distal end of the elongate shaft 302 as the counter-pivoting mechanism 306 is actuated (e.g., from the configuration of FIG. 8A to the configuration of FIG. 8B) although their relative position will change (i.e., translate).

Because the control cables 356 are helically wrapped around the elongate tube approximately 180°, the control cable extending along the right side of the links 307a-d is the same control cable that extends along the left side of the links 315a-d. In this regard, one control cable is configured to pass through the right side of joint 309b, the control able wraps helically around the elongate tube 314, and the control able exists the elongate tube 314 at the left side of joint 311a, which may reduce the actuation force needed to actuate the counter-pivoting mechanism 306 or may multiply the force applied, as compared to designs in which the control cables extend substantially straight through the counter-pivoting mechanism without helically wrapping. Helical wrapping of the control cables 356 may also increase the stiffness of the joints in the counter-pivoting mechanism 306.

In the illustrated example of FIG. 8B, the control cables 356 have been actuated in such a manner that the joints 309*a* and 311*b* have remained in their neutral position. However, it will be appreciated that joints 309*a* and 311*b* could be actuated in a pitch direction instead of joints 309*b* and 311*a* being actuated in a yaw direction, or all of joints 309*a-b*, 311*a-b* could be simultaneously actuated to provide pitch and yaw movements, while maintaining the parallel alignment of anchor link 342 and adapter 308. In this illustrated example, the inner joints 309*b* and 311*a* have parallel axes of rotation and the outer joints 309*a* and 311*b* have parallel axes of rotation such that the inner joints mirror one another and the outer joints mirror one another. It will be appreciated that in some examples, the joints may be arranged in number of alternate configurations. For example, the proximal joint 309*a* of the proximal joint assembly could be arranged parallel to the proximal joint 311*a* of the distal joint assembly and the distal joint 309*b* of the proximal joint assembly arranged parallel to the distal joint 311*b* of the distal joint assembly.

A plurality of control cables 356 may be actuated simultaneously to cause a desired movement of the counter-pivoting mechanism 306. For example, in an example in which the control cables 356 are arranged in pairs of opposing cables (e.g., separated by 180°) a first control cable may be pulled (e.g., length decreased) while an opposing second control cable is released (e.g., length increased) at substantially the same rate, resulting in cable length conservation. In some examples, each control cable may be actuated by a separate actuator. In some examples, opposing control cables may be actuated by a single actuator with the proximal ends of each control cable wrapped around a capstan in opposing directions with the capstan configured for rotation by the actuator. Cable length conservation may facilitate maintaining a desired tension in the control cables to prevent derailing of a slack cable and/or excessive tension in the cables which may damage the cables or other components.

Figure 9:
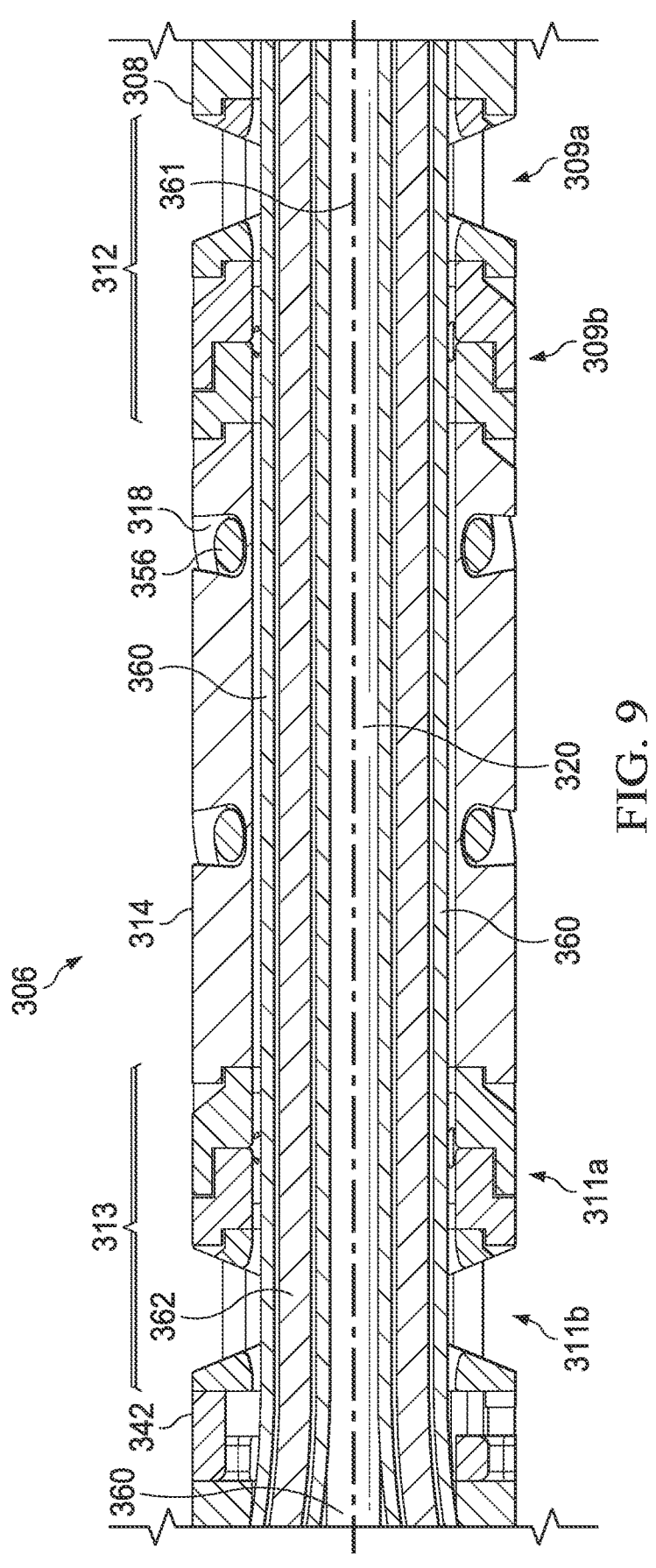
FIG. 9 illustrates a cross-section through a distal portion of an instrument in accordance with the present disclosure.

FIG. 9 illustrates a cross-section taken along the longitudinal axis 361 of the elongate tube 314 of the counter-pivoting mechanism 306. As described above, a plurality of wrist and/or end effector control members (e.g., cables) may extend through the central lumen 320 of the counter-pivoting mechanism 306. As further described above, optionally, coil pipes 360 may additionally extend through the central lumen 320 of the counter-pivoting mechanism 306. The coil pipes 360 may surround or house the wrist and/or end effector control cables 362 while isolating axial loading caused by actuation of the wrist and/or control cables 362 from the counter-pivoting mechanism 306 so as to prevent the counter-pivoting mechanism 306 from bending in response to actuating forces on the wrist control cables 362. Conversely, the coil pipes 360 may also prevent the counter-pivoting mechanism 306 from exerting a force on the wrist control cables 362 when the counter-pivoting mechanism 306 is actuated which would otherwise tend to manipulate the wrist.

Figures 10, 11:
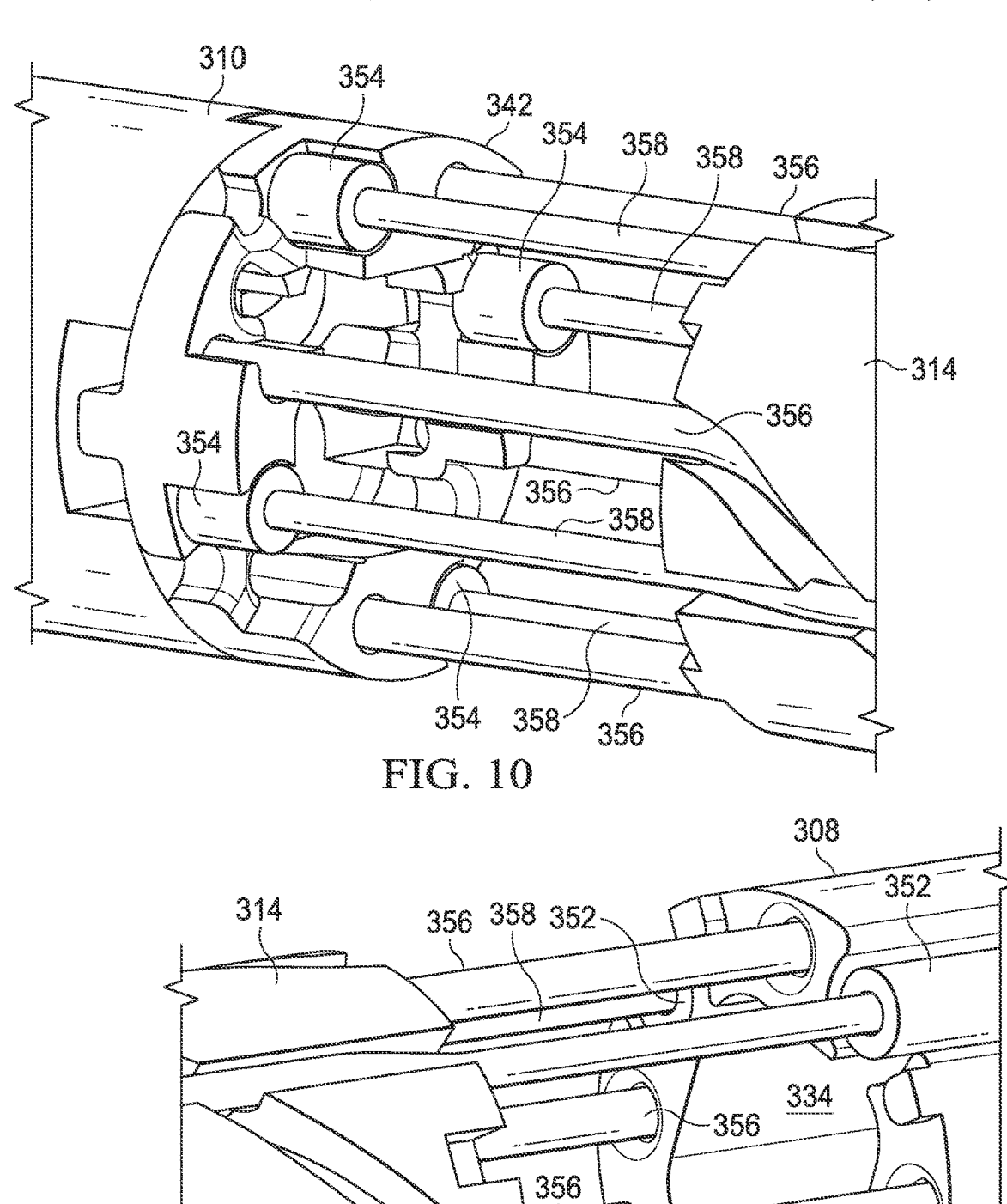
FIG. 10 illustrates a distal end of a counter-pivoting mechanism in accordance with the present disclosure with links removed.
FIG. 11 illustrates a proximal end of a counter-pivoting mechanism in accordance with the present disclosure with links removed.

FIGS. 10-11 illustrate the distal and proximal ends, respectively, of the counter-pivoting mechanism 306 with the links 307, 315 removed to avoid obscuring other features. At the distal end shown in FIG. 10, as described above in relation to FIGS. 7A-7B, the distal anchors 354 of the constraint cables 358 may be received in anchor recesses on the proximal side of the anchor link 342. In some examples, the distal anchors 354 may be secured to the anchor link 342 and/or the distal link 315*d* while in other examples, the distal anchors 354 may be secured only to the constraint cables

358 themselves to prevent the distal ends of the constraint cables from being withdrawn through the constraint cable lumens 332 in the distal link 315*d*. The control cables 356 may pass through the control cable lumens 348 in the anchor link 342 and are anchored distally thereof. In some examples, the control cables 356 are tied off around a component of the anchor link 342, such the supports 346. In some examples, each of the control cables 356 is secured to an anchor, similar to the distal anchors 354, on either the proximal side or the distal side of the anchor link 342 with anchor recesses (e.g., anchor recess 350 of FIG. 7A) housing the anchors. In some examples, the anchor link 342 may be omitted and the distal anchors 354 on the constraint cables 358 and similar anchors on the control cables 356 may rest against the distal side of the distal most link of the distal joint assembly (e.g., distal link 315*d* in FIG. 8A). In some examples, the distal anchors 354 on the constraint cables 358 and similar anchors on the control cables 356 may be received in anchor recesses (similar to anchor recesses 340 in the adapter 308 shown in FIG. 6) formed into proximal end of a wrist component (e.g., proximal wrist link 305*a*) or other component of the instrument 300 disposed distal of the counter-pivoting mechanism 306.

At the proximal end of the counter-pivoting mechanism 306, as shown in FIG. 11, the proximal anchors 352 of the constraint cables 358 may be received in anchor recesses in the adapter 308. In some examples, the proximal anchors 352 may be secured to the adapter 308 and/or the proximal link 307*a* while in other examples, the proximal anchors 352 may be secured only to the constraint cables 358 themselves and may abut the proximal link 307*a* to prevent the proximal ends of the constraint cables from being withdrawn through the constraint cable lumens 332 in the proximal link 307*a*. The control cables 356 pass through the control cable lumens (lumens 338 in FIG. 6) in the adapter 308 and extend through the elongate shaft 302.

In the illustrated example, the control cable lumens in the anchor link 342 and adapter 308 are aligned with the second grooves 318 on the elongate tube 314 such that the control cables extend linearly through the proximal joint assembly 312 from the adapter 308 to the elongate tube 314 and from the elongate tube 314 to the anchor link 342 through the distal joint assembly 313, while the control cables wrap helically through the elongate tube 314. In contrast, the constraint cables 358 are positioned radially inward at the anchor link 342 and adapter 308 as compared to their position in the first grooves 316 on the elongate tube 314. With the links 307, 315 removed, this can be seen in FIGS. 10 and 11 as a slight curvature in the constraint cables 358 proximal of the proximal end of the elongate tube 314 and distal of the distal end of the elongate tube 314. This arrangement may bias the constraint cables 358 radially inward in the elongate tube 314 which may aid in retaining the control cables 356 in their respective grooves.

It will be appreciated that in other examples, the control cables 356 and/or the constraint cables 358 may be positioned radially inward or radially outward in one or more components of the counter-pivoting mechanism 306 (e.g., the elongate tube 314, in the joint assemblies 312,313, in the adapter 308, and/or in the anchor link 342) from their respective positions shown in the illustrated example.

Figure 12:
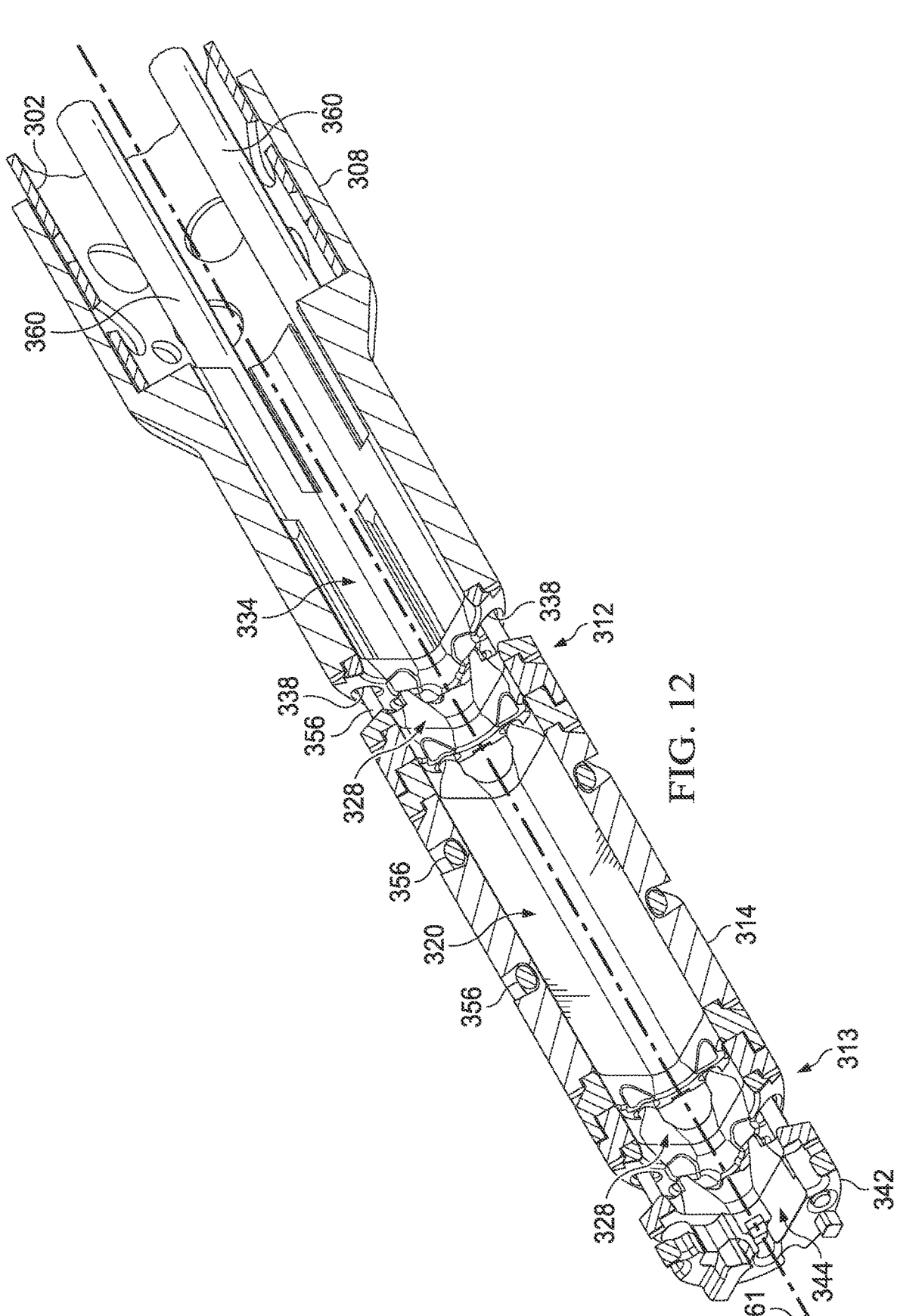
FIG. 12 illustrates a cross-section through a distal portion of an instrument in accordance with the present disclosure.

FIG. 12 illustrates a cross-section of the counter-pivoting mechanism 306 along the longitudinal axis with the wrist control cables 362 and their respective coil pipes 360 removed from the central lumens 320, 328, 334, 344 of the various components to avoid obscuring other features. Although the coil pipes for the wrist control cables 362 are not shown, two of the four coil pipes 360 for the control cables 356 are shown extending along the length of the elongate shaft 302 and terminating in the adapter 308. From the distal ends of the coil pipes 360, the control cables 356 extend through the control cable lumens 338 of the adapter 308. Although the illustrated example and the description thereof includes four control cables 356 and four constraint cables 358, it should be appreciated that any suitable number of control cables 356 or constraint cables 358 may be used.

Figure 13A:
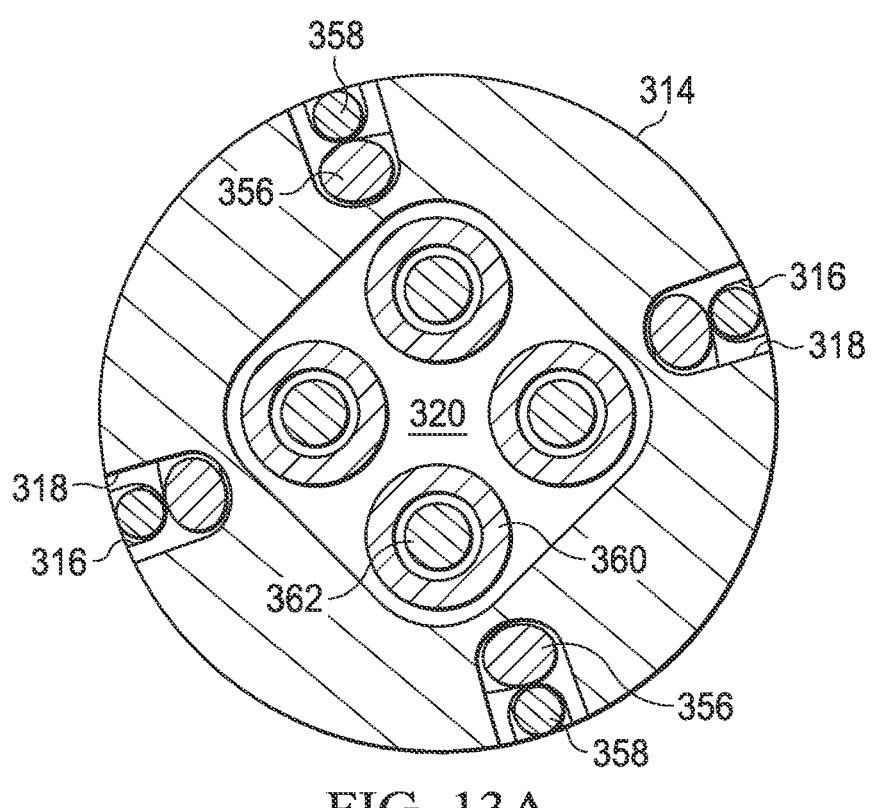
FIGS. 13A-13B illustrate transverse cross-sections through the counter-pivoting mechanism of FIG. 9.
Figure 13B:
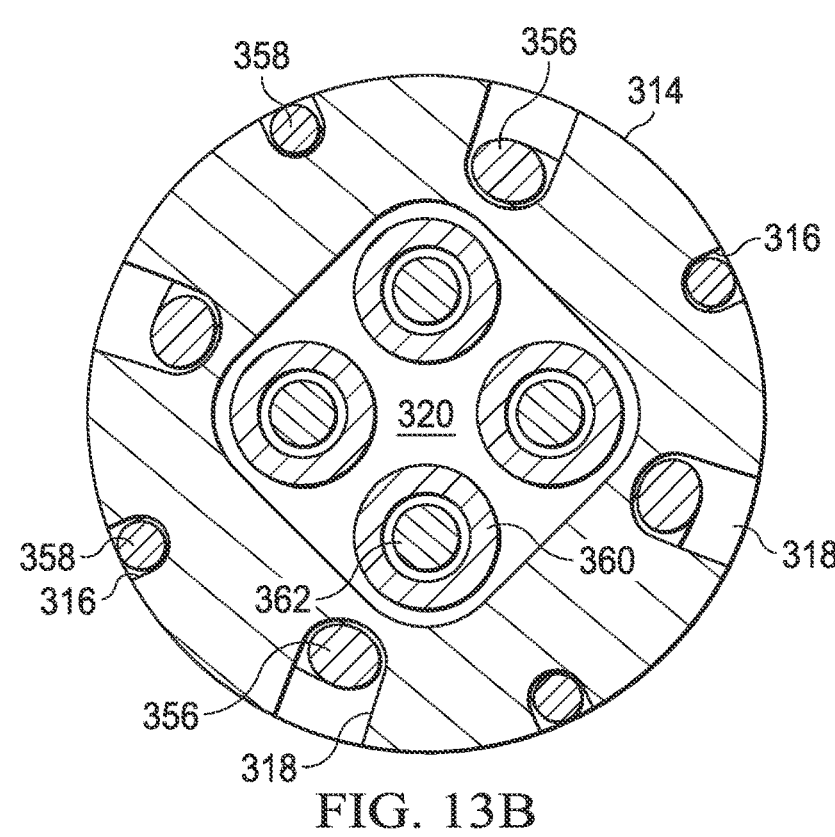

FIGS. 13A and 13B show cross-sections taken through the elongate tube 314 in planes transverse to the longitudinal axis and separated by a distance along the length of the elongate tube 314. It can be seen that four wrist control cables 362 and their respective coil pipes 360 extend through the central lumen 320. It is contemplated that the coil pipes 360 for the wrist control cables 362 could be removed, allowing the central lumen 320 and, in turn, the outer diameter of the elongate tube 314 to be made smaller. Providing four wrist control cables 362 as shown may allow for control of a number of degrees of freedom of the wrist assembly 310 and end effector 304. For example, in the case of a gripper as shown in FIG. 3, four wrist control cables 362 may allow for control in 3 degrees of freedom including pitch, yaw, and opening/closing the jaws.

At the cross-section shown in FIG. 13A, the plurality of first grooves 316 circumferentially coincide with the plurality of second grooves 318 such that the constraint cables 358 cross over the control cables 356. At the cross-section shown in FIG. 13B, the plurality of first grooves 316 are circumferentially offset from the plurality of second grooves 318. It will be appreciated that this distinction between FIGS. 13A and 13B is due to the first grooves 316 being substantially linear along the elongate tube 314 while the second grooves 318 helically wrap around the elongate tube 314, as shown for example in FIG. 4.

Although not shown in FIGS. 13A-13B, it is contemplated that a shape sensor, such as a fiber optic shape sensor, could extend through the counter-pivoting mechanism 306 to measure bend angles of the joints 309, 311, the wrist assembly 310, and/or the end effector 304. Such a shape sensor could either be routed through the central lumen of each component of the counter-pivoting mechanism 306 (e.g., central lumen 320 of the elongate tube 314) or through a lumen formed within the wall of each component similar to the routing of the control cables.

Additionally or alternatively to the wrist control cables 362, one or more conductor wires could be routed through the central lumens to provide power to the end effector as may be needed for an electrically powered end effector such as an ablation tool or imaging device. Similarly, one or more control rods for pushing or pulling to actuate an end effector such as a gripper could be routed through the central lumens.

Figure 14:
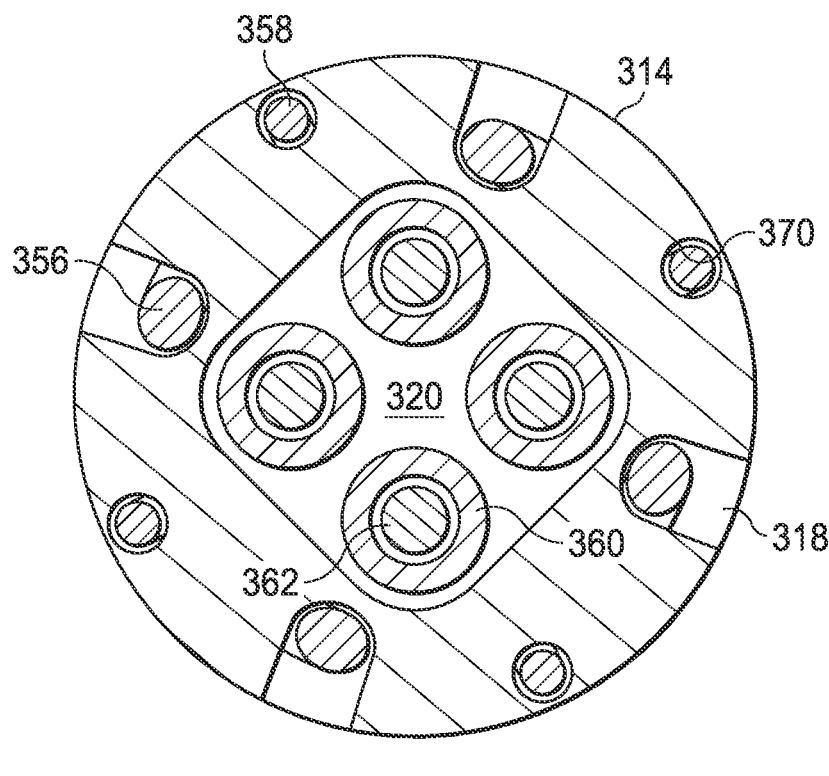
FIGS. 14-16 illustrate transverse cross-sections through examples of counter-pivoting mechanisms in accordance with the present disclosure.
Figure 15:
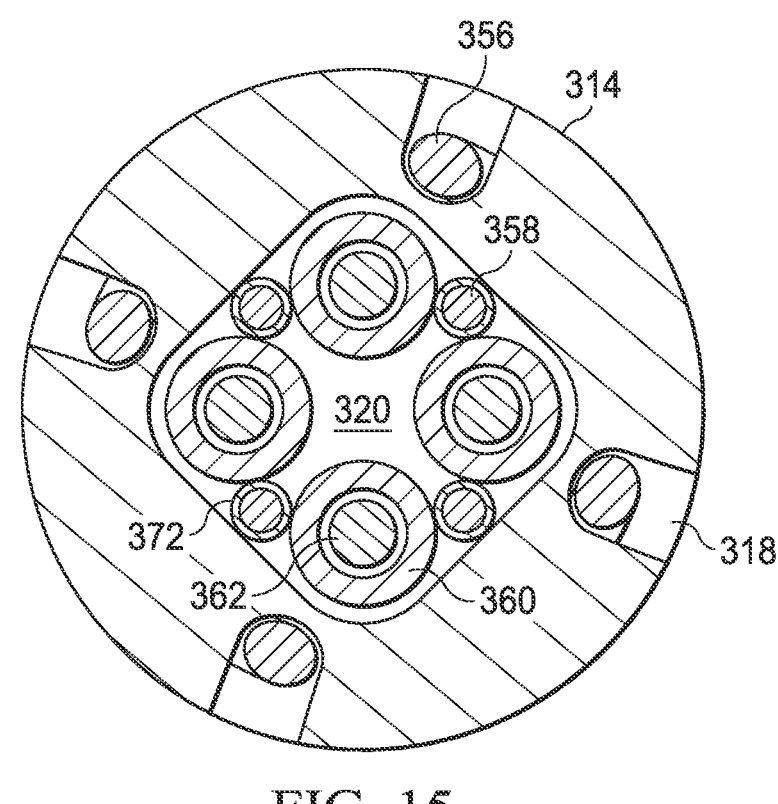
Figure 16:
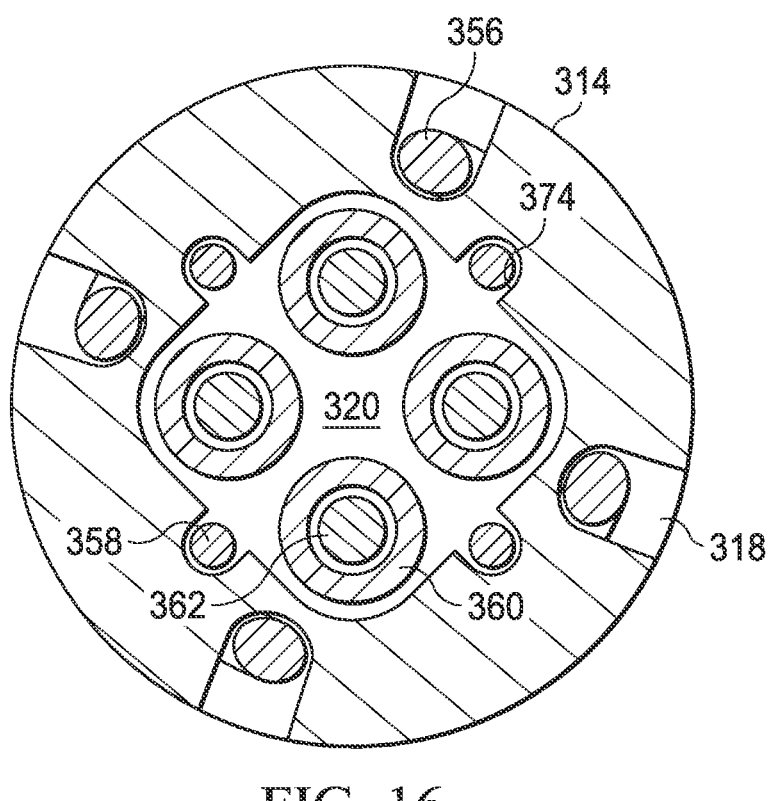

FIGS. 14-16 illustrate cross-sectional views of various alternative arrangements of the elongate tube 314 of the counter-pivoting mechanism 306. In FIG. 14, as compared to FIG. 13B, the plurality of first grooves 316 are replaced by a plurality of channels in the form of constraint cable lumens 370 formed in the wall of the elongate tube 314 such that the constraint cables 358 extend through the constraint cable lumens 370. In FIG. 15, the plurality of first grooves 316 are replaced by a plurality of channels comprising constraint cable tubes 372, which may comprise or be similar to coil pipes, such that the constraint cables 358 extend through the constraint cable tubes 372 within the central lumen 320. Optionally, the constraint cable tubes 372 may be omitted. In FIG. 16, the plurality of first grooves 316 are replaced by a plurality of channels comprising constraint cable grooves 374 formed on an internal surface of the elongate tube 314 within the central lumen 320 such that the constraint cables 358 extend within the constraint cable grooves 374. As discussed above in relation to FIGS. 10-11, the constraint cables 358 may be positioned radially inward within the constraint cable grooves 374 as compared to the location of the constraint cables 358 within the joint assemblies 312, 313. In this regard, the constraint cables 358 may be biased outward within the elongate tube 314 which may help retain the constraint cables 358 within the constraint cable grooves 374.

In some examples, a method of manufacturing a counter-pivoting mechanism 306 or an instrument 300 with a counter-pivoting mechanism may include forming an elongate tube 314. The elongate tube may be constructed of any suitable material(s) providing sufficient rigidity to resist bending including, but not limited to, ceramic, plastic, thermoplastic, polyvinyl chloride (PVC), polyamide-imide (PAI), polyetheretherketone (PEEK), polyethylene terephthalate (PET), polycarbonate, acrylic, steel, stainless steel, titanium, aluminum, cobalt, nickel, molybdenum, chromium, metal alloy, etc. The elongate tube may be constructed using one or more of a variety of manufacturing processes including, but not limited to, injection molding, casting, negative manufacturing processes such as machining, and/or additive manufacturing processes such as fused deposition modeling, powder bed sintering, etc.

In some examples, the elongate tube 314 is formed from a cylindrical blank workpiece of stock material. The stock may be a round tube or solid rod. If needed, a central lumen 320 may be formed, for example by machining, along the longitudinal axis of the blank. One or more sets of grooves and/or channels may be formed through a wall of the workpiece, into an outer surface of the workpiece, or into an inner surface of the workpiece defining the central lumen, for example by machining or milling. In an example, two sets of grooves are formed in the outer surface of the workpiece. A first set of grooves 316 is formed linearly along a length of the tube parallel to the longitudinal axis and a second set of grooves 318 is formed helically around the workpiece using, for example, a 4-axis CNC mill. The second set of grooves may be milled deeper into the workpiece than the first set of grooves, or vice versa.

In some examples, the elongate tube 314 is formed from a powdered material using additive manufacturing. In an example, a laser or electron beam may be controlled to melt regions of successive layers of the powdered material in a powder bed. In another example, a polymer may be used to fuse layers of the powdered material together. The piece may then be heated, for example in a furnace, to melt the polymer out of the piece and sinter the remaining powder together. Additive manufacturing may be preferred in examples in which machining may be difficult, for example, those in which channels for receiving cables are formed as lumens extending axially or helically within a wall of the elongate tube or as grooves extending along an inner surface of the elongate tube forming the central lumen.

In some examples, a combination of negative and additive manufacturing processes may be used to form an elongate tube 314.

Links 307 may be also constructed using any suitable negative or additive manufacturing process(es). Joints 309 may be constructed by matingly engaging first mating features 319a and corresponding second mating features 319b of link pairs. Joints may then be assembled together to form a proximal joint assembly 312 and a distal joint assembly 313 by mating a plurality of protrusions 322 and a corresponding plurality of recesses 324 on adjacent joints. An adhesive may be used to secured adjacent joints together.

The joint assemblies 312, 313 may be secured to the elongate tube 314 by a snap-fit between corresponding mating protrusions 322 and recesses 324 and/or an adhesive. If present, an anchor link 342 may be secured to a distal end of the distal joint assembly 313 in a similar manner. Similarly, the distal joint assembly 313 or anchor link 342 (if present) may be secured to the wrist assembly 310 (present) or to an end effector 304 and the proximal joint assembly 312 may be secured to the elongate shaft 302 or to an adapter 308.

A method of manufacturing a counter-pivoting mechanism 306 or an instrument 300 with a counter-pivoting mechanism may further include routing a set of constraint cables 358 through a first set of grooves or channels in the elongate tube 314 and routing a set of control cables 356 through a second set of grooves or channels in the elongate tube. In examples in which both the constraint cables and control cables are disposed in sets of grooves formed into an outer surface of the elongate tube with one set of grooves being deeper than the other, the cables corresponding to the deeper grooves (e.g., control cables) may be inserted first followed by the cables corresponding to the shallower grooves (e.g., constraint cables). Such examples may improve efficiency and reduce overall assembly time by allowing the cables to be inserted into the elongate tube radially in a direction transverse to the longitudinal axis as compared to threading each cable longitudinally through a channel in the elongate tube.

The control cables 356 and constraint cables 358 may be routed through the various components of the instrument 300 at any suitable step in the assembly processes. In an example, the control cables 356 and constraint cables 358 may first be routed through the elongate tube 314 and the proximal and distal joint assemblies 312, 313 (or each separate link thereof) may be slid over the respective ends of the control cables and constraint cables with the cables passing through corresponding lumens in each link 307. Proximal anchors 352 may be secured to the proximal ends of the constraint cables 358 and distal anchors 354 may be secured to the distal ends of the constraint cables 358. The distal ends of the control cables 356 may be secured to the distal end of the counter-pivoting mechanism 306 (e.g., at the anchor link 342). The proximal ends of the control cables 356 may then be fed into the elongate shaft 302 before securing the counter-pivoting mechanism 306 thereto. In another example, both the control cables 356 and the constraint cables 358 are fed through the counter-pivoting mechanism 306 after assembly of the elongate tube 314 to the proximal and distal joint assembly 312, 313 and before securing the counter-pivoting mechanism 306 to the elongate shaft 302. In another example, the constraint cables 358 are routed through the counter-pivoting mechanism 306 and secured thereto with proximal and distal anchors 352, 354, then the counter-pivoting mechanism 306 is secured to the elongate shaft 302, and then the control cables are routed through the counter-pivoting mechanism 306 and secured to the distal end thereof (e.g., at the distal side of the anchor link 342).

Distal end control mechanisms including wrist assembly control cables, end effector control cables, or other end effector devices such electrical wires for electrocautery, ablation, imaging, etc., each of which may optionally be disposed in a coil pipe, may be routed through the central lumens 320, 328, and 334 when securing the wrist assembly 310 and/or end effector 304 to the counter-pivoting mechanism 306. This may occur prior or subsequent to securing the counter-pivoting mechanism 306 to the elongate shaft 302.

In the description, specific details have been set forth describing some examples. Numerous specific details are set forth in order to provide a thorough understanding of the examples. It will be apparent, however, to one skilled in the art that some examples may be practiced without some or all of these specific details. The specific examples disclosed herein are meant to be illustrative but not limiting. One skilled in the art may realize other elements that, although not specifically described here, are within the scope and the spirit of this disclosure.

Elements described in detail with reference to one example, example, implementation, or application optionally may be included, whenever practical, in other examples, implementations, or applications in which they are not specifically shown or described. For example, if an element is described in detail with reference to one example and is not described with reference to a second example, the element may nevertheless be claimed as included in the second example. Thus, to avoid unnecessary repetition in the foregoing description, one or more elements shown and described in association with one example, implementation, or application may be incorporated into other examples, implementations, or application unless specifically described otherwise, unless the one or more elements would make an example or implementation non-functional, or unless two or more of the elements provide conflicting functions. Similarly, it should be understood that any particular element, including a system component or a method process, is optional and is not considered to be an essential feature of the present disclosure unless expressly stated otherwise.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one example may be combined with the features, components, and/or steps described with respect to other examples of the present disclosure. In addition, dimensions provided herein are for specific examples and it is contemplated that different sizes, dimensions, and/or ratios may be utilized to implement the concepts of the present disclosure.

While some examples are provided herein in the context of medical procedures, any reference to medical or surgical instruments and medical or surgical methods is non-limiting. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy) and performing procedures on human or animal cadavers. Further, these techniques may also be used for surgical and nonsurgical medical treatment or diagnosis procedures.

The methods described herein are illustrated as a set of operations or processes. Not all the illustrated processes may be performed in all examples of the methods. Additionally, one or more processes that are not expressly illustrated or described may be included before, after, in between, or as part of the example processes. In some examples, one or more of the processes may be performed by the control system (e.g., control system 112) or may be implemented, at least in part, in the form of executable code stored on non-transitory, tangible, machine-readable media that when run by one or more processors (e.g., processors of control system 112) may cause the one or more processors to perform one or more of the processes.

One or more elements in examples of this disclosure may be implemented in software to execute on a processor of a computer system such as control processing system. When implemented in software, the elements of the examples of the present disclosure are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc. Any of a wide variety of centralized or distributed data processing architectures may be employed. Programmed instructions may be implemented as a number of separate programs or subroutines, or they may be integrated into a number of other aspects of the systems described herein. In one example, the control system supports wireless communication protocols such as Bluetooth, IrDA, HomeRF, IEEE 802.11, DECT, and Wireless Telemetry.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the examples of the present disclosure are not described with reference to any particular programming language. It will be appreciated that a variety of programming languages may be used to implement the teachings of the present disclosure.

This disclosure describes various instruments, portions of instruments, and anatomic structures in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). The "pitch" direction and "yaw" direction are not necessarily limited to vertical and horizontal movement, respectively, but rather may be arbitrary directions orthogonal to one another. As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along a length of an object.

While certain exemplary examples of the present disclosure have been described and shown in the accompanying drawings, it is to be understood that such examples are merely illustrative of and not restrictive on the broad disclosure herein, and that the examples of the present disclosure should not be limited to the specific constructions and arrangements shown and described, since various other modifications may occur to those ordinarily skilled in the art.

What is claimed is:

1. An instrument comprising:
an elongate shaft having a proximal portion and a distal portion;
a counter-pivoting mechanism comprising:
a first joint coupled to the distal portion of the elongate shaft, the first joint comprising a first link;
a second joint disposed distally of the first joint, the second joint comprising a second link;
an elongate tube disposed between the first joint and the second joint and having a central lumen extending along a longitudinal axis of the elongate tube; and
a plurality of constraint cables extending between the first and second joints within a plurality of first grooves formed in an outer circumferential surface of a wall of the elongate tube; and
a plurality of control cables extending through the elongate shaft and configured to control manipulation of the counter-pivoting mechanism, wherein the plurality of control cables wraps helically around at least a portion of the elongate tube within a plurality of second grooves formed in the outer circumferential surface of the wall of the elongate tube,
wherein the first and second joints are coupled by the plurality of constraint cables such that as the counter-pivoting mechanism is manipulated by the plurality of control cables, the first joint pivots in a first direction as the second joint pivots in a second direction opposite the first direction while the first link and the second link are maintained in a parallel orientation.

2. The instrument of claim 1, wherein each of the plurality of control cables is secured to the second joint.

3. The instrument of claim 1, further comprising:
a third joint coupled to the first joint; and
a fourth joint coupled to the second joint, wherein the first and second joints are configured to pivot in a pitch direction and wherein the third and fourth joints are configured to pivot in a yaw direction.

4. The instrument of claim 3, wherein the plurality of control cables comprises a set of pitch control cables and a set of yaw control cables.

5. The instrument of claim 1, wherein each control cable of the plurality of control cables exits the wall of the elongate tube at a position circumferentially offset approximately 180° with respect to the longitudinal axis from a position in which each respective control cable enters the wall of the elongate tube.

6. The instrument of claim 1, wherein the plurality of second grooves is formed deeper into the wall than the plurality of first grooves such that the plurality of constraint cables is disposed radially outward from the plurality of control cables within the elongate tube.

7. The instrument of claim 1, wherein the plurality of first grooves is formed deeper into the wall than the plurality of second grooves such that the plurality of constraint cables is disposed radially inward from the plurality of control cables within the elongate tube.

8. The instrument of claim 1, wherein an outer diameter of the elongate tube is less than about 6 mm.

9. The instrument of claim 8, wherein a maximum width of the central lumen is greater than about 2.5 mm.

10. The instrument of claim 1, wherein a ratio of a cross-sectional area of the central lumen to a cross-sectional area of the elongate tube is greater than 1:2.

11. The instrument of claim 1, further comprising an end effector disposed distally of the counter-pivoting mechanism.

12. The instrument of claim 11, wherein the end effector includes a wrist joint.

13. The instrument of claim 12, wherein a plurality of wrist control cables extend through the central lumen of the elongate tube and are secured to the wrist joint.

14. The instrument of claim 13, wherein the plurality of wrist control cables is disposed within a plurality of coil pipes extending through the central lumen of the elongate tube.

15. The instrument of claim 13, wherein the end effector comprises a gripper and the plurality of wrist control cables comprises at least four cables configured to control pitch, yaw, and grip of the end effector.

16. The instrument of claim 11, wherein the end effector comprises an electrocautery blade or an ablation tool, and a conductor wire extends through the central lumen of the elongate tube.

17. The instrument of claim 1, further comprising a shape sensor extending through the first and second joints.

18. The instrument of claim 6, wherein the plurality of first grooves intersect the plurality of second grooves.

19. The instrument of claim 11, wherein the end effector comprises a gripper and a plurality of grip control cables extend through the central lumen of the elongate tube and are secured to the gripper.

20. A method of controlling an instrument comprising:

manipulating at least one control cable of a plurality of control cables extending through an elongate shaft of the instrument, the instrument having a proximal portion, a distal portion, and a counter-pivoting mechanism, the counter-pivoting mechanism comprising:

a first joint coupled to the distal portion of the elongate shaft, the first joint comprising a first link;

a second joint disposed distally of the first joint, the second joint comprising a second link;

an elongate tube disposed between the first joint and the second joint and having a central lumen extending along a longitudinal axis of the elongate tube; and a plurality of constraint cables extending linearly between the first and second joints within a plurality of first grooves formed in an outer circumferential surface of a wall of the elongate tube, wherein the at least one control cable extends through at least one of a plurality of helically wrapped second grooves formed in an outer circumferential surface of a wall of the elongate tube;

wherein manipulating the at least one control cable causes the first joint to pivot in a first direction and the second joint to pivot in a second direction opposite the first direction while the first link and the second link are maintained in a parallel orientation by the plurality of constraint cables.

\* \* \* \* \*